US012611264B2

(12) United States Patent
Zhao

(10) Patent No.: US 12,611,264 B2
(45) **Date of Patent: \*Apr. 28, 2026**

(54) SYSTEMS AND METHODS OF REGISTRATION FOR IMAGE-GUIDED PROCEDURES

(71) Applicant: INTUITIVE SURGICAL OPERATIONS, INC., Sunnyvale, CA (US)

(72) Inventor: Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/812,551

(22) Filed: Aug. 22, 2024

(65) Prior Publication Data

US 2024/0407860 A1      Dec. 12, 2024

Related U.S. Application Data

(63) Continuation of application No. 18/322,410, filed on May 23, 2023, now Pat. No. 12,096,996, which is a
(Continued)

(51) Int. Cl.
*A61B 34/20*          (2016.01)
*A61B 34/35*          (2016.01)
(Continued)

(52) U.S. Cl.
CPC .............. *A61B 34/20* (2016.02); *A61B 34/35* (2016.02); *A61B 1/00045* (2013.01);
(Continued)

(58) Field of Classification Search
CPC ..... A61B 34/20; A61B 34/35; A61B 1/00045; A61B 1/2676; A61B 2034/2051;
(Continued)

(56) References Cited

U.S. PATENT DOCUMENTS 4,695,697 A      9/1987 Kosa
6,379,304 B1 *   4/2002 Gilbert ................ G01S 15/8934
                                                              600/447
(Continued)

FOREIGN PATENT DOCUMENTS

CN          1853573 A      11/2006
CN          102657531 A     9/2012
(Continued)

OTHER PUBLICATIONS

Extended European Search Report for Application No. 18748440.7 mailed on Nov. 19, 2020, 8 pages.
(Continued)

*Primary Examiner* — Sanjay Cattungal
(74) *Attorney, Agent, or Firm* — Haynes & Boone, LLC.

(57) ABSTRACT

Systems and methods for supporting image-guided procedures include a device having an instrument usable to collect location data for one or more passageways and one or more processors coupled to the instrument. The one or more processors are configured to organize a plurality of points within the location data based on a corresponding insertion depth of the instrument when each of the plurality of points is collected, create a passageway tree based on the points, identify at least three non-collinear landmark locations within the passageway tree, create a seed transformation between one or more of the at least three non-collinear landmark locations and corresponding model locations in model data, and register, using the seed transformation, the plurality of points to the model data for the one or more passageways. In some embodiments, the at least three non-collinear landmark locations are based on a main branch point in the passageway tree.

20 Claims, 12 Drawing Sheets

Related U.S. Application Data continuation of application No. 16/482,020, filed as application No. PCT/US2018/016390 on Feb. 1, 2018, now Pat. No. 11,690,678.

(60) Provisional application No. 62/453,401, filed on Feb. 1, 2017.

(51) Int. Cl.
 *A61B 1/00* (2006.01)
 *A61B 1/267* (2006.01)

(52) U.S. Cl.
 CPC ..... *A61B 1/2676* (2013.01); *A61B 2034/2051* (2016.02); *A61B 2034/2055* (2016.02); *A61B 2034/2065* (2016.02)

(58) Field of Classification Search
 CPC .... A61B 2034/2055; A61B 2034/2065; A61B 2034/2061
 See application file for complete search history.

(56) References Cited

U.S. PATENT DOCUMENTS

| | | | |
|---|---|---|---|
| 6,380,732 B1 | 4/2002 | Gilboa | |
| 6,389,187 B1 | 5/2002 | Greenaway et al. | |
| 6,468,212 B1* | 10/2002 | Scott ..................... | A61B 8/463 600/440 |
| 7,316,681 B2 | 1/2008 | Madhani et al. | |
| 7,772,541 B2 | 8/2010 | Froggatt et al. | |
| 7,781,724 B2 | 8/2010 | Childers et al. | |
| 8,050,523 B2 | 11/2011 | Younge et al. | |
| 8,900,131 B2 | 12/2014 | Chopra et al. | |
| 11,690,678 B2 | 7/2023 | Zhao | |
| 2005/0182295 A1 | 8/2005 | Soper et al. | |
| 2006/0013523 A1 | 1/2006 | Childlers et al. | |
| 2007/0185476 A1 | 8/2007 | Maksimovich | |
| 2008/0242999 A1* | 10/2008 | Kakee ................. | G01S 7/52046 600/458 |
| 2008/0319317 A1* | 12/2008 | Kamiyama ......... | G01S 7/52077 600/443 |
| 2010/0082041 A1 | 4/2010 | Prisco | |
| 2010/0232666 A1 | 9/2010 | Urban et al. | |
| 2011/0245675 A1* | 10/2011 | Yoshida ................. | A61B 8/466 600/443 |
| 2013/0096377 A1 | 4/2013 | Duindam et al. | |
| 2013/0197365 A1* | 8/2013 | Baba ....................... | A61B 8/54 600/447 |
| 2013/0223702 A1 | 8/2013 | Holsing et al. | |
| 2013/0237825 A1* | 9/2013 | Sasaki ...................... | G06T 5/40 600/443 |
| 2013/0303890 A1 | 11/2013 | Duindam et al. | |
| 2013/0303893 A1 | 11/2013 | Duindam et al. | |
| 2014/0058406 A1 | 2/2014 | Tsekos | |
| 2014/0343416 A1 | 11/2014 | Panescu et al. | |
| 2014/0378837 A1* | 12/2014 | Fujiwara ............... | A61B 8/463 600/443 |
| 2015/0193932 A1* | 7/2015 | Hashimoto ............ | A61B 8/466 382/132 |
| 2017/0112472 A1* | 4/2017 | Song .................... | A61B 8/0833 |
| 2017/0209071 A1 | 7/2017 | Zhao et al. | |
| 2020/0275949 A1* | 9/2020 | Masotti ................ | A61B 8/5292 |
| 2020/0297442 A1 | 9/2020 | Adebar et al. | |
| 2023/0301725 A1 | 9/2023 | Zhao | |

FOREIGN PATENT DOCUMENTS

| | | |
|---|---|---|
| CN | 103548054 A | 1/2014 |
| WO | WO-2010111090 A1 | 9/2010 |
| WO | WO-2016164311 A1 | 10/2016 |
| WO | WO-2016191298 A1 | 12/2016 |

OTHER PUBLICATIONS

International Preliminary Report on Patentability for Application No. PCT/US2018/016390, mailed on Aug. 15, 2019, 06 pages.
International Search Report and Written Opinion for application No. PCT/US2018/016390, Mailed on May 11, 2018, 9 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

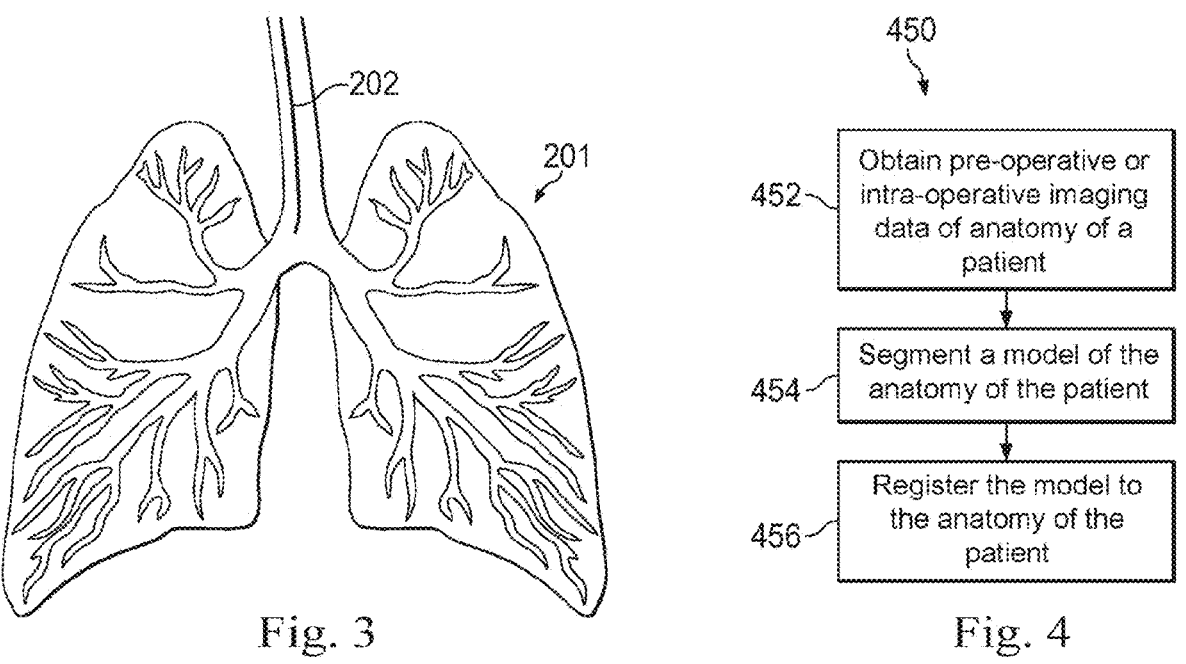
202
201
Fig. 3
450
| 452 | Obtain pre-operative or intra-operative imaging data of anatomy of a patient |
| 454 | Segment a model of the anatomy of the patient |
| 456 | Register the model to the anatomy of the patient |
Fig. 4
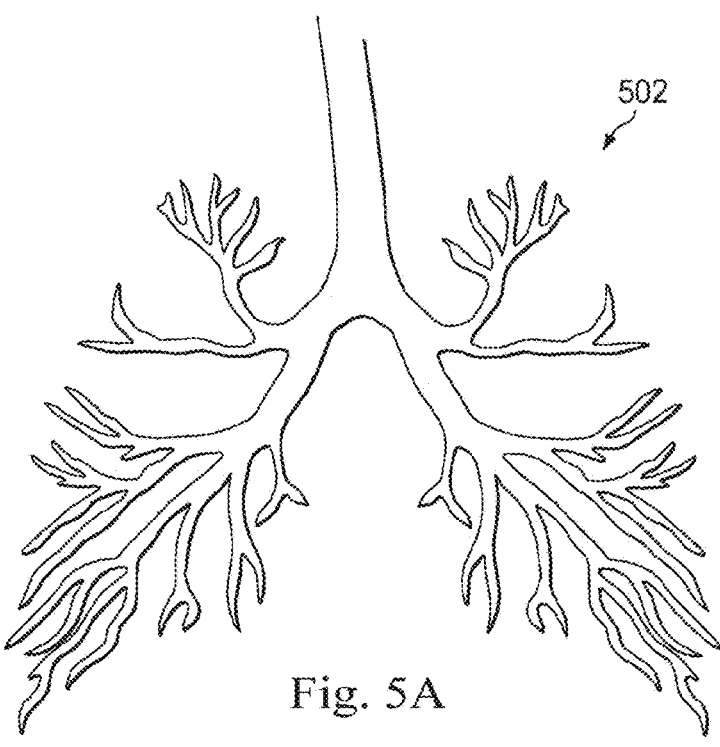
502
Fig. 5A

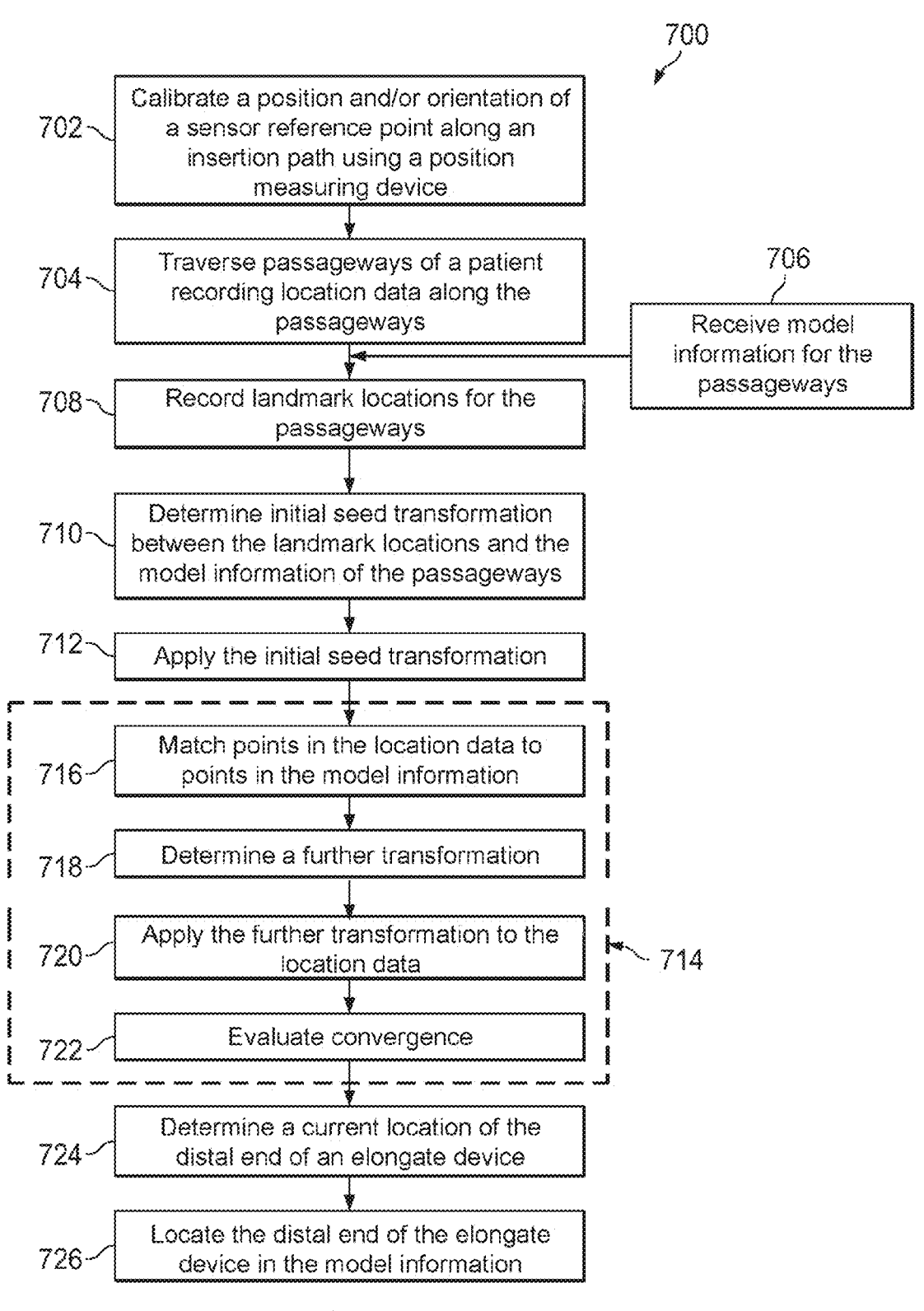

700

702 — Calibrate a position and/or orientation of a sensor reference point along an insertion path using a position measuring device 704 — Traverse passageways of a patient recording location data along the passageways 706 — Receive model information for the passageways 708 — Record landmark locations for the passageways 710 — Determine initial seed transformation between the landmark locations and the model information of the passageways 712 — Apply the initial seed transformation 716 — Match points in the location data to points in the model information 718 — Determine a further transformation 720 — Apply the further transformation to the location data 722 — Evaluate convergence

714

724 — Determine a current location of the distal end of an elongate device

726 — Locate the distal end of the elongate device in the model information

Fig. 7

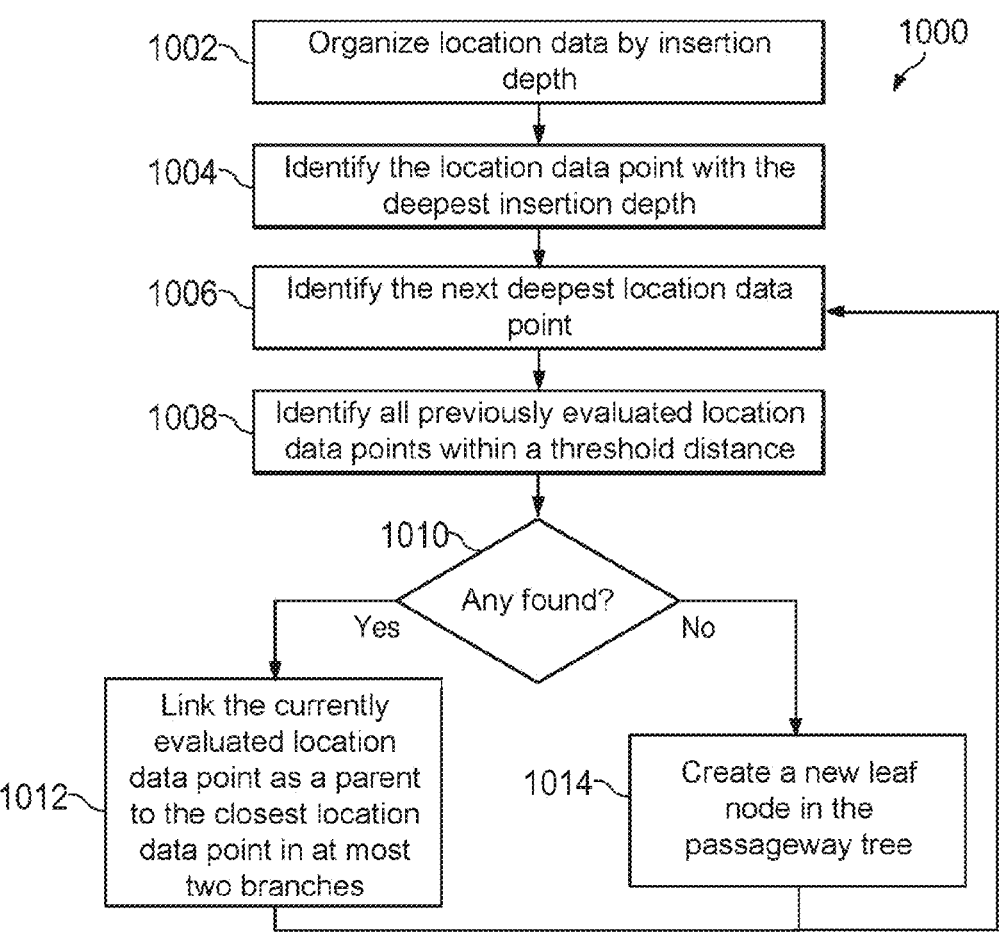

1002 — Organize location data by insertion depth

1004 — Identify the location data point with the deepest insertion depth

1006 — Identify the next deepest location data point

1008 — Identify all previously evaluated location data points within a threshold distance 1010 — Any found?

Yes — 1012 — Link the currently evaluated location data point as a parent to the closest location data point in at most two branches No — 1014 — Create a new leaf node in the passageway tree

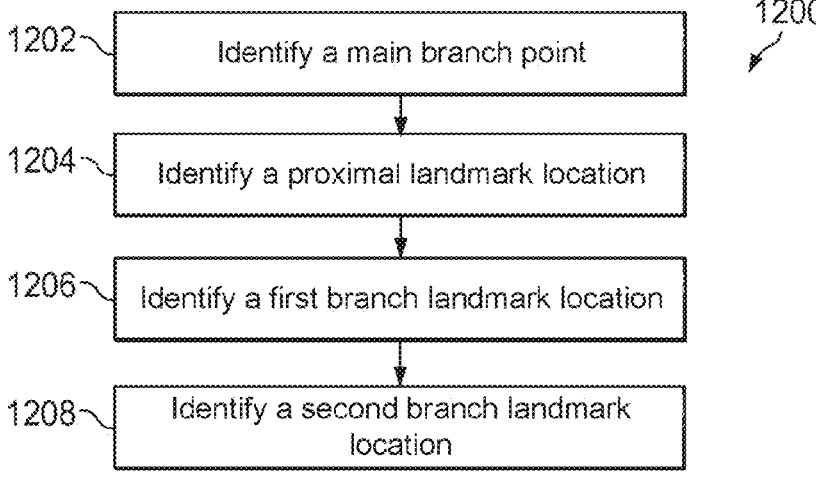

1202 — Identify a main branch point

1204 — Identify a proximal landmark location

1206 — Identify a first branch landmark location

1208 — Identify a second branch landmark location

Additional
Passageway
Tree

SYSTEMS AND METHODS OF REGISTRATION FOR IMAGE-GUIDED PROCEDURES

RELATED APPLICATIONS

This patent application is a continuation of U.S. patent application Ser. No. 18/322,410, filed May 23, 2023, which is a continuation of U.S. patent application Ser. No. 16/482, 020 (now U.S. Pat. No. 11,690,678), filed Jul. 30, 2019, which is the U.S. national phase of International Application No. PCT/US2018/016390, filed Feb. 1, 2018, which designated the U.S. and claims priority to and the benefit of the filing date of U.S. Provisional Patent Application No. 62/453,401, entitled "Systems and Methods of Registration for Image-Guided Surgery," filed Feb. 1, 2017, all of which are incorporated by reference herein in their entirety.

FIELD

The present disclosure is directed to systems and methods for conducting an image-guided procedure, and more particularly to registration during an image-guided procedure.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. Traditional instrument tracking and referencing systems may require the use of patient pads during pre-operative and operative imaging and may disturb the clinical environment or workflow. Systems and methods for performing image-guided surgery with minimal clinical disturbances are needed.

SUMMARY

The embodiments of the invention are best summarized by the claims that follow the description.

Consistent with some embodiments, a device includes an instrument usable to collect location data for one or more passageways and one or more processors coupled to the instrument. The one or more processors are configured to organize a plurality of points within the location data based on a corresponding insertion depth of the instrument when each of the plurality of points is collected, create a passageway tree based on the organized points, identify at least three non-collinear landmark locations within the passageway tree, create a seed transformation between one or more of the at least three non-collinear landmark locations and corresponding model locations in model data, and register, using the seed transformation, the plurality of points to the model data for the one or more passageways.

Consistent with some embodiments, to identify the at least three non-collinear landmark locations within the passageway tree, the one or more processors are further configured to identify a main branch point in the passageway tree, identify a first landmark location proximal to the main branch point, identify a second landmark location distal to the main branch point in a first branch of the passageway tree distal to the main branch point, and identify a third landmark location distal to the main branch point in a second branch of the passageway tree distal to the main branch point, the second branch being different from the first branch.

Consistent with some embodiments, a method of registration using one or more processors includes collecting a set of sensor data during insertion a flexible elongate device within a plurality of passageways, wherein the sensor data comprises a plurality of points representing a plurality of locations of a flexible elongate device within the plurality of passageways, organizing the plurality of points based on a corresponding insertion depth of the flexible elongate device when each of the plurality of points is collected, creating a passageway tree based on the organized points, identifying at least three non-collinear landmark locations within the passageway tree, creating a seed transformation between the one or more of the at least three non-collinear landmark locations and corresponding model locations in model data, and registering, using the seed transformation, the plurality of points to the model data for the plurality of passageways.

Consistent with some embodiments, identifying the at least three non-collinear landmark locations includes identifying a main branch point in the passageway tree, identifying a first landmark location proximal to the main branch point, identifying a second landmark location distal to the main branch point in a first branch of the passageway tree, wherein the first branch is distal to the main branch point, and identifying a third landmark location distal to the main branch point in a second branch of the passageway tree, wherein the second branch is distal to the main branch point, the second branch being different from the first branch.

Consistent with some embodiments, a non-transitory machine-readable medium includes a plurality of machine-readable instructions which when executed by one or more processors associated with a device are adapted to cause the one or more processors to perform any of the methods described herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 3 illustrates an exemplary medical instrument positioned within an anatomic passageway of a human lung.

FIG. 4 illustrates a flowchart of an exemplary method to provide guidance in an image-guided surgical procedure.

Figure 5B:
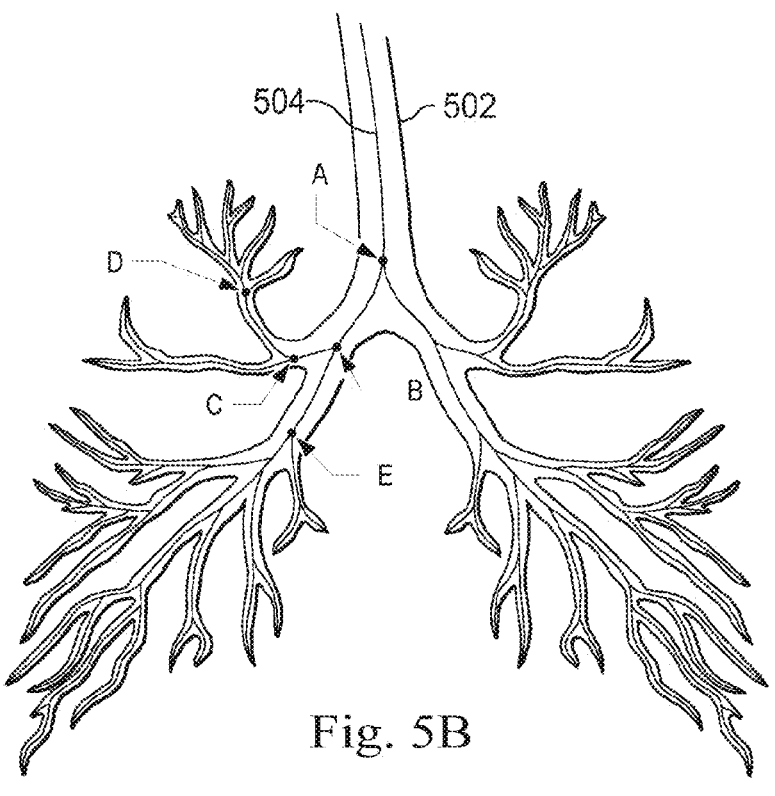
Figure 5C:
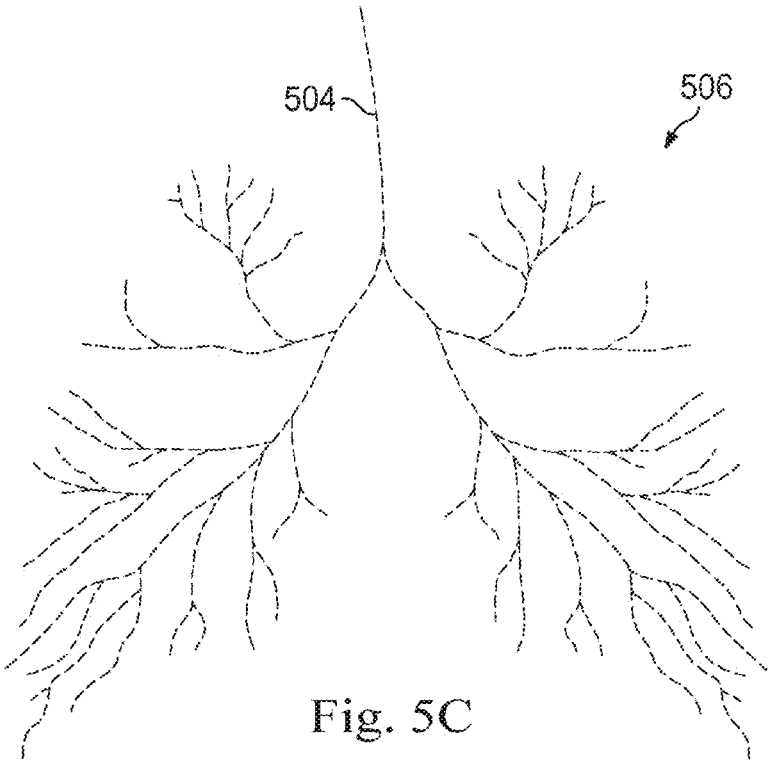

FIGS. 5A, 5B, and 5C illustrate exemplary application of processes in a segmentation method that generates a model of human lungs for registration.

Figure 6A:
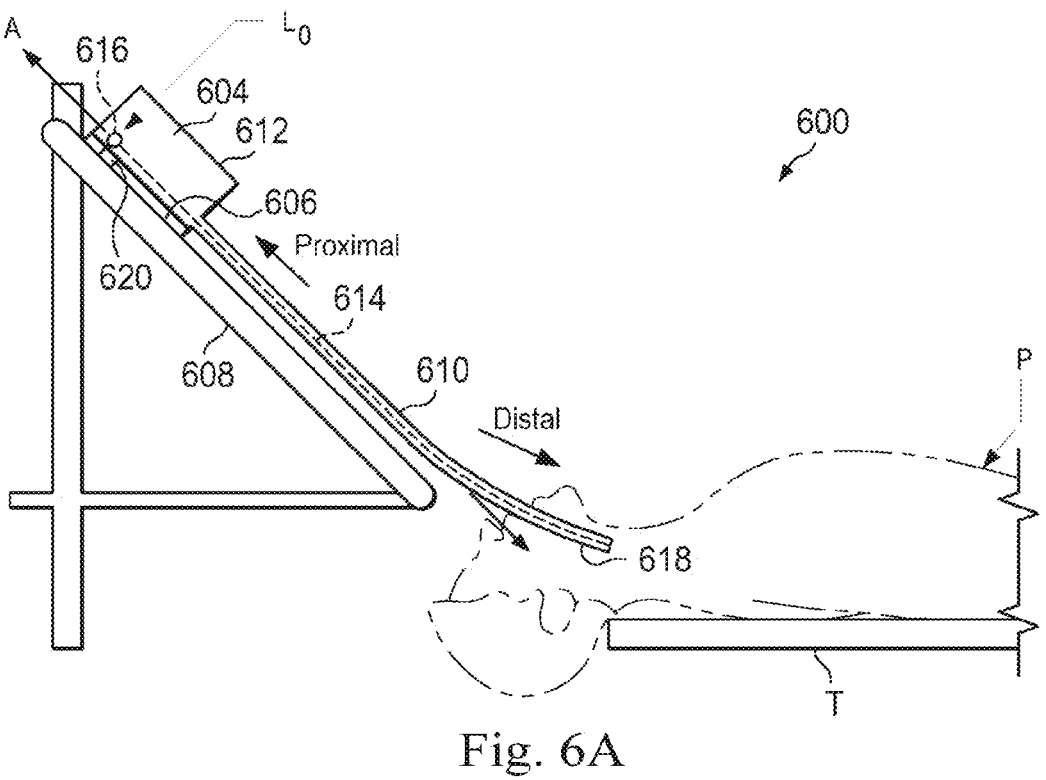
Figure 6B:
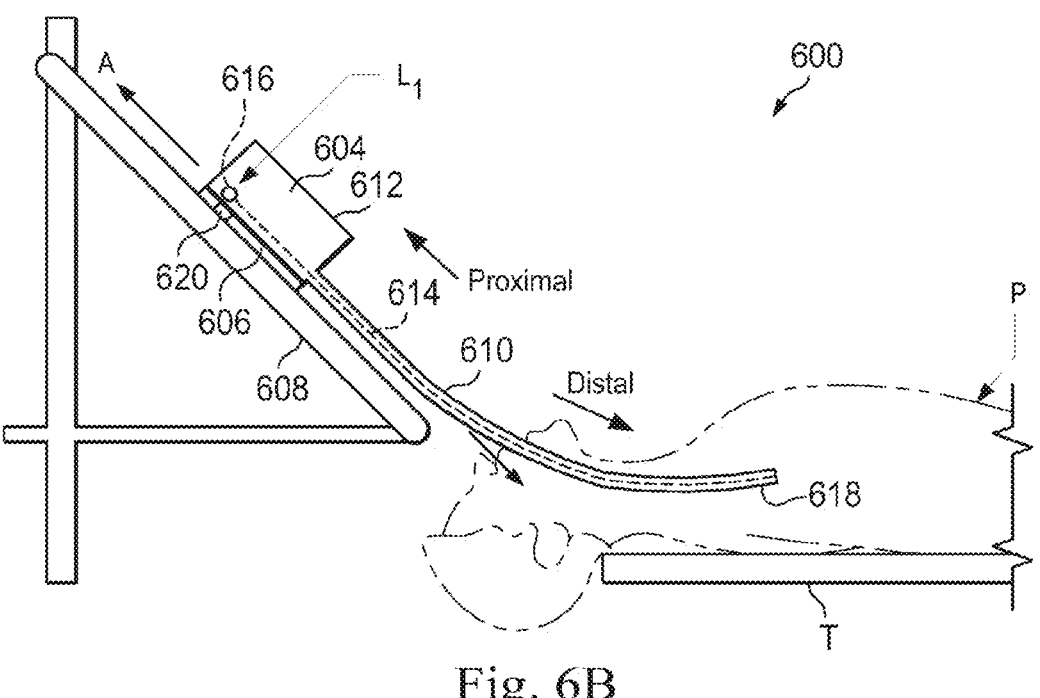

FIGS. 6A and 6B are exemplary side views of a patient coordinate space including a medical instrument mounted on an insertion assembly.

Figure 6C:
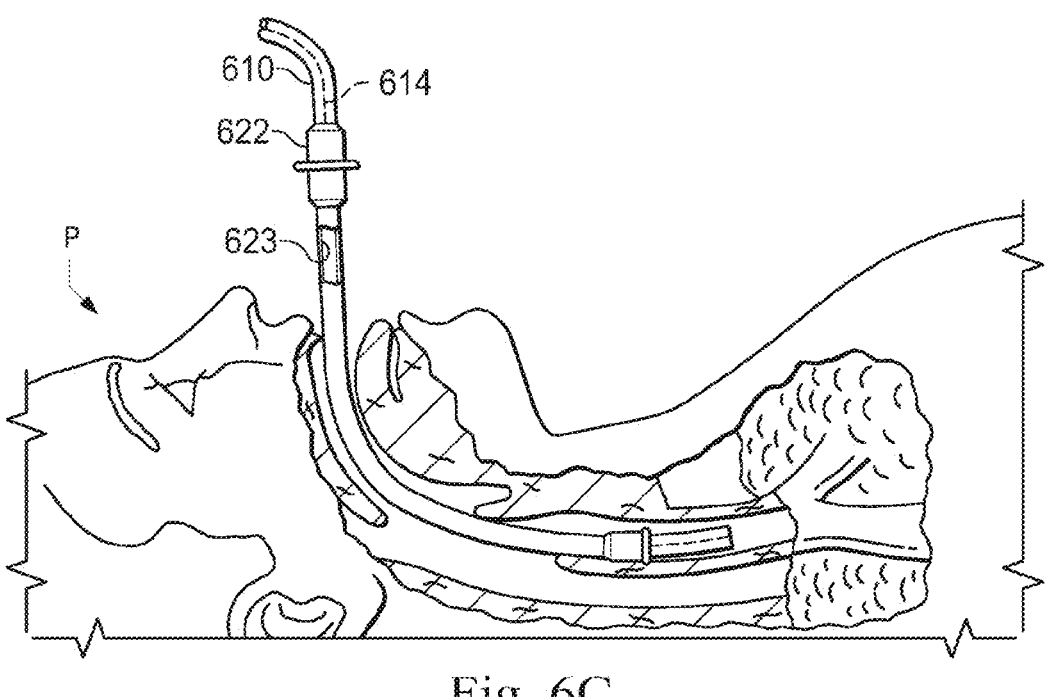

FIG. 6C is an exemplary side view of a patient in a patient coordinate space including an endotracheal tube.

FIG. 7 illustrates a flowchart of an exemplary method of providing guidance for an image-guided surgical procedure.

Figure 8:
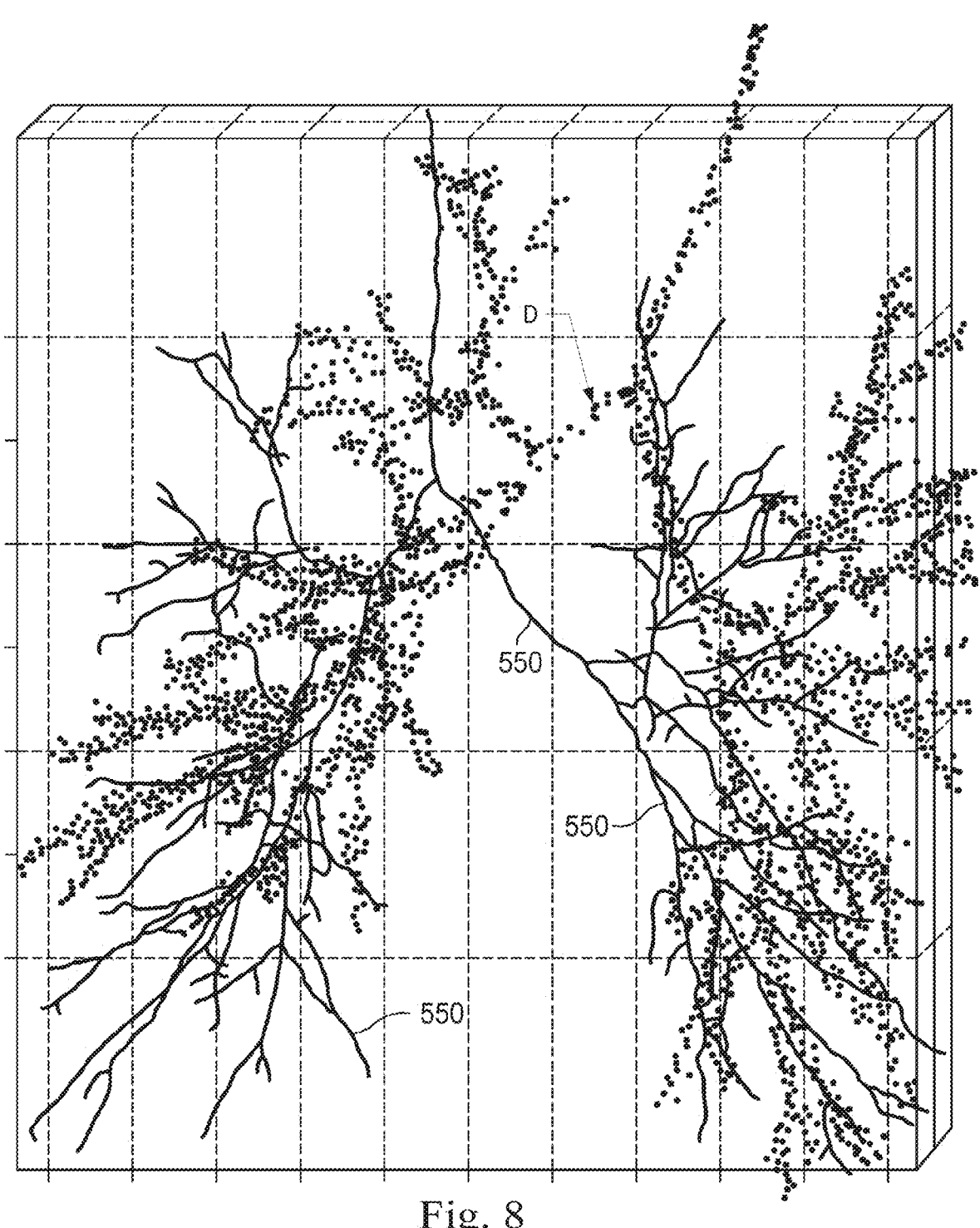

FIG. 8 illustrates exemplary location data collected by traversing airways in human lungs.

Figure 9:
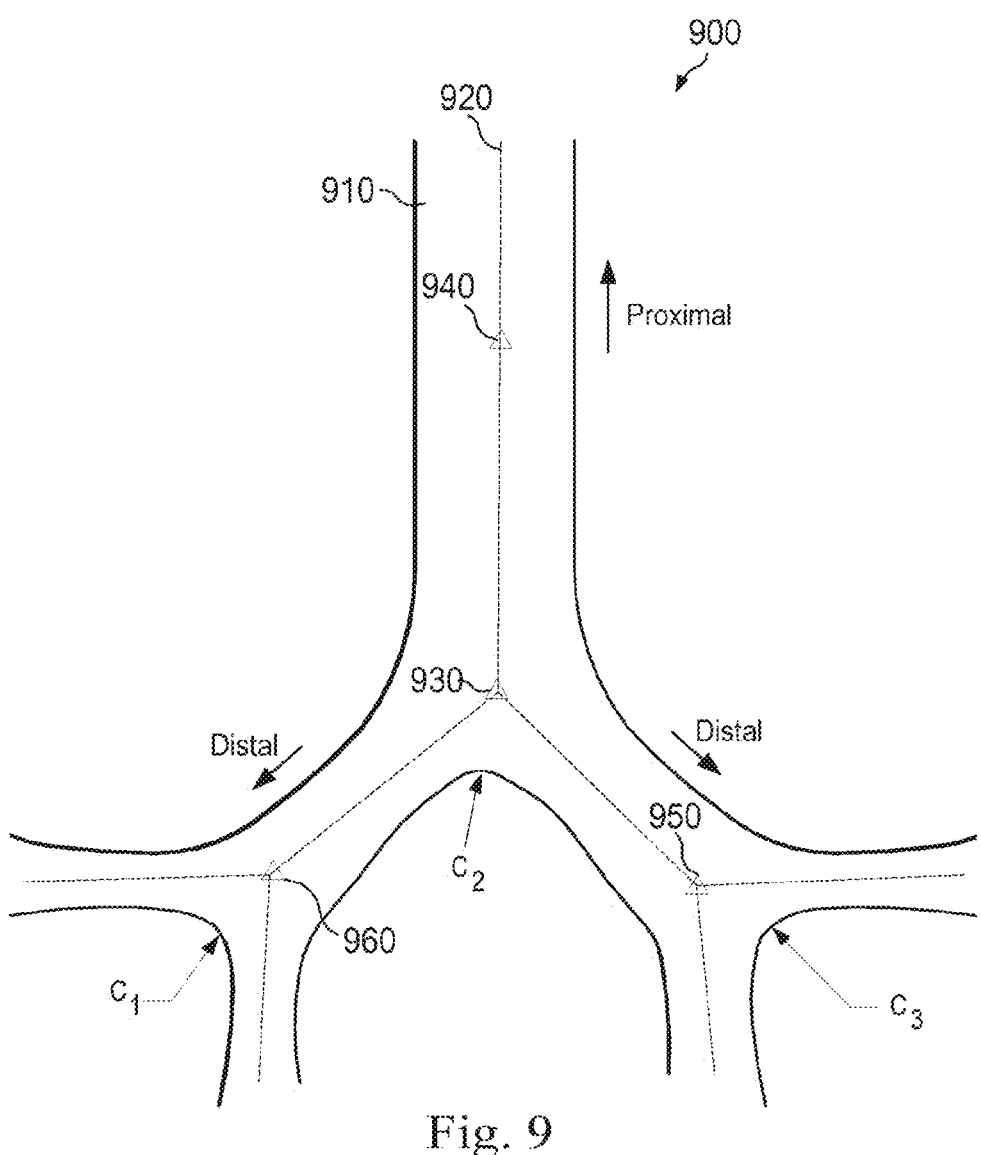

FIG. 9 illustrates exemplary landmark locations for airways in human lungs.

FIG. 10 illustrates a flowchart of an exemplary method of building a passageway tree in location data.

Figure 11A:
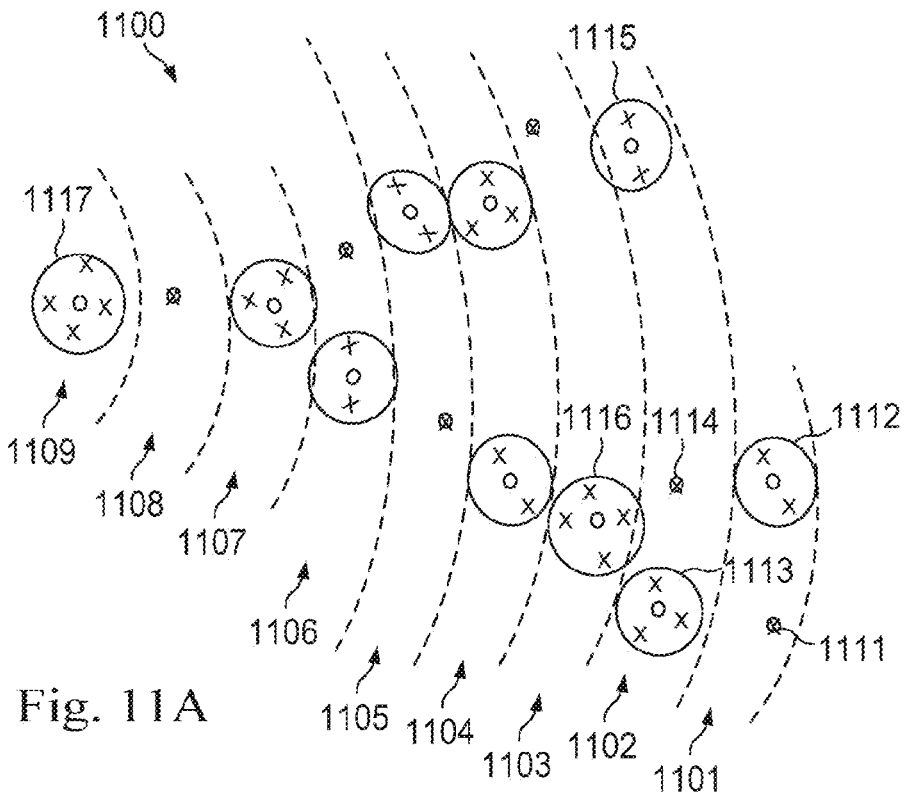

FIG. 11A illustrates application of the method of FIG. 10 on exemplary location data.

Figure 11B:
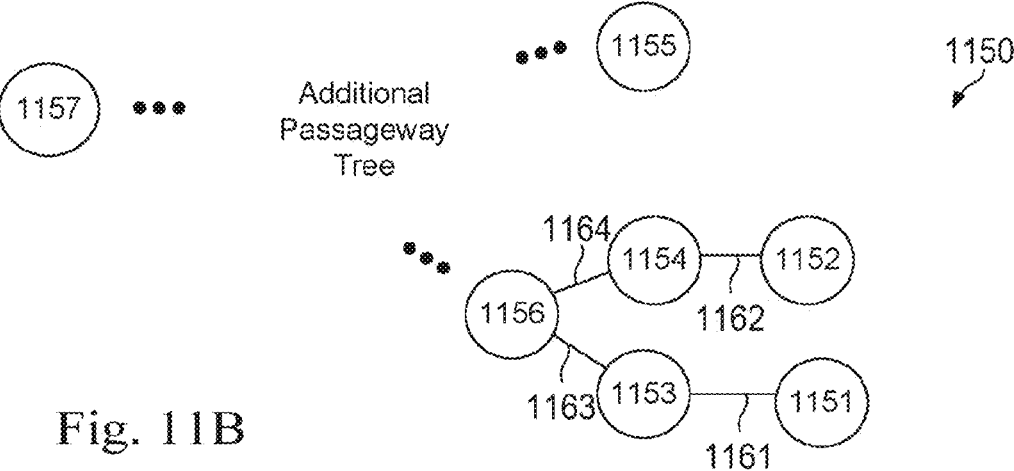

FIG. 11B illustrates the passageway tree resulting from the exemplary location data of FIG. 11A.

FIG. 12 illustrates a flowchart of an exemplary method of identifying landmark locations from a passageway tree.

Figure 13:
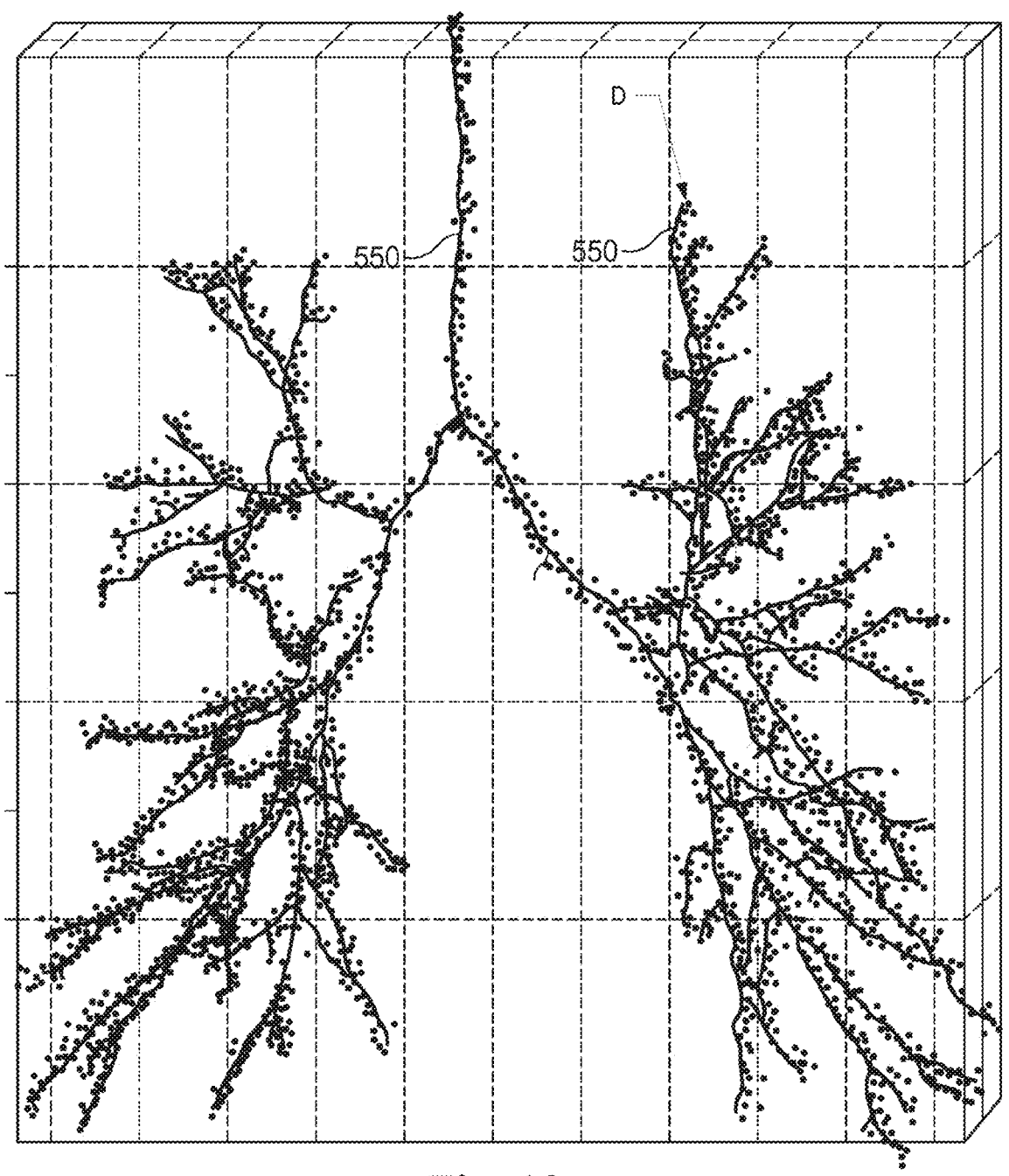

FIG. 13 illustrates an exemplary post registration alignment of two sets of points resulting from application of an exemplary registration technique.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

This disclosure focuses primarily on embodiments where the passageways being traversed are airways in lungs. However, one of ordinary skill in the art would understand that these disclosures are equally applicable to other types of passageways that include one or more branch points. For example, other suitable anatomic passageways include vasculature, renal calyces, lymphatic vessels, and/or the like. In other examples, the passageways may correspond to non-anatomic passageways including sewer tunnels, plumbing pipes, conduits, heating ventilation and air conditioning (HVAC) ducts, mines, caves, and/or the like.

Figure 1:
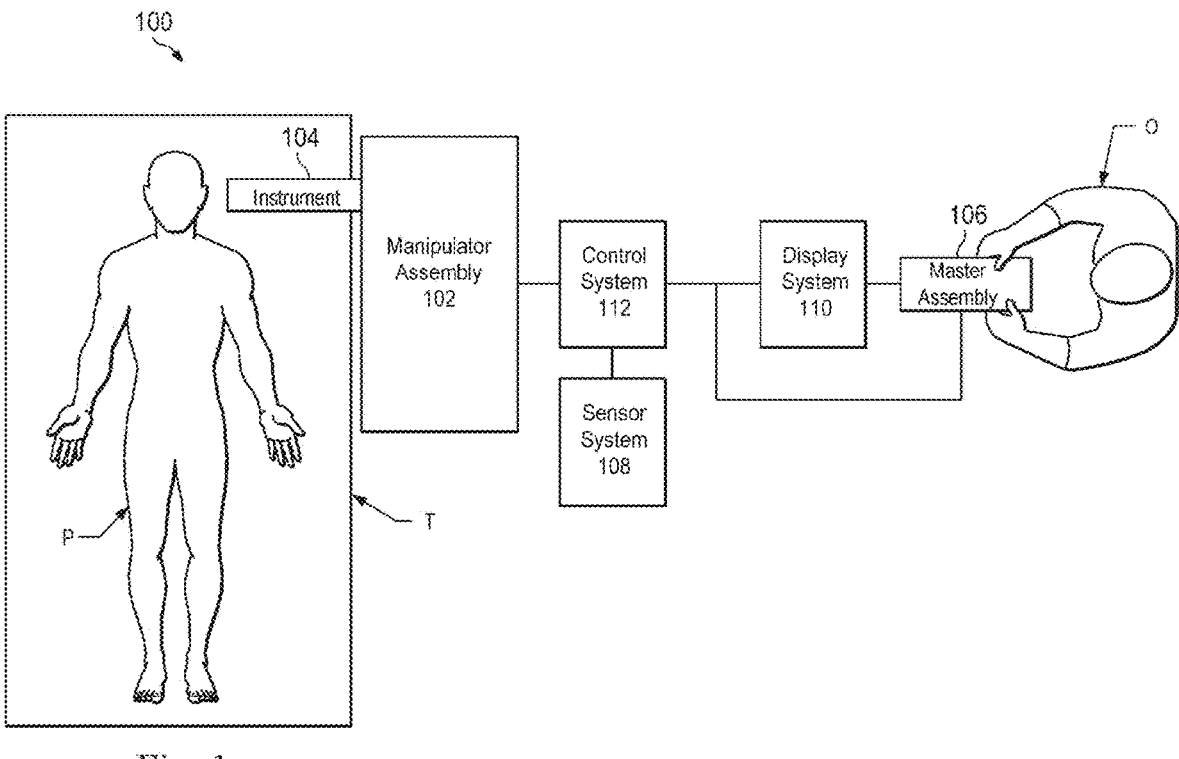
FIG. 1 is an exemplary teleoperated medical system.

FIG. 1 is an exemplary teleoperated medical system 100. In some embodiments, teleoperated medical system 100 may be suitable for use in, for example, surgical, diagnostic, therapeutic, or biopsy procedures. As shown in FIG. 1, medical system 100 generally includes a manipulator assembly 102 for operating a medical instrument 104 in performing various procedures on a patient P. Manipulator assembly 102 is mounted to or near an operating table T. A master assembly 106 allows an operator O (e.g., a surgeon, a clinician, or a physician as illustrated in FIG. 1) to view the interventional site and to control manipulator assembly 102.

Master assembly 106 may be located at a operator's console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intraoperatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one non-teleoperational manipulator assembly, more than one teleoperational manipulator assembly, and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more manipulator assemblies in various combinations.

Figures 2A, 2B:
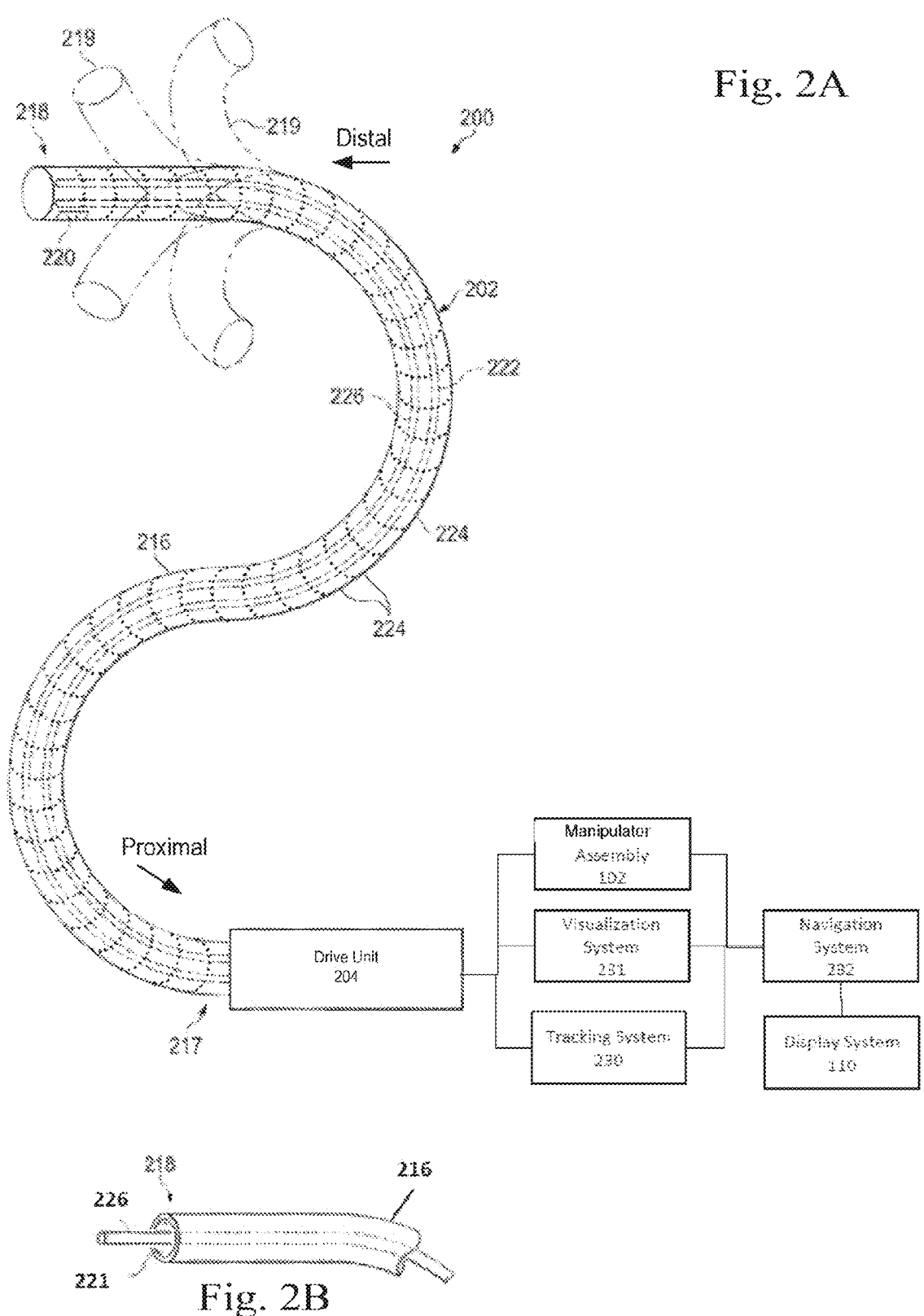
FIG. 2A illustrates an exemplary medical instrument system.
FIG. 2B illustrates an exemplary medical instrument with an extended medical tool.

FIG. 2A is an exemplary medical instrument system 200. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 m. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is an exemplary flexible body 216 with medical instrument 226 extended. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

FIG. 3 illustrates an exemplary medical instrument in the form of elongate device 202 positioned within an anatomic passageway of a human lung 201. In some embodiments, elongate device 202 may be used in other passageways of an anatomy.

FIG. 4 illustrates a flowchart of an exemplary method 450 for use in an image-guided surgical procedure. At process 452, pre-operative or intra-operative image data of the anatomy of a patient is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent human lungs 201 of FIG. 3.

At a process 454, a segmented model of the anatomy of the patient is determined. Using computer software alone or in combination with manual input is used to convert the recorded images into a segmented two-dimensional or three-dimensional composite representation or model of a partial or an entire anatomic organ or anatomic region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as a marching cube function, to generate a 3D surface that encloses the voxels. In some examples, the model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

At a process 456, the model is registered to the patient anatomy. In some examples, the registering may occur prior to and/or during the course of an image-guided surgical procedure on the patient. Generally, registration involves the matching of measured points to points of the model through the use of rigid and/or non-rigid transforms. Measured points may be generated using landmarks in the anatomy, electromagnetic coils scanned and tracked during the procedure, and/or a shape sensor system. The measured points may be generated for use in an iterative closest point (ICP) technique as described in further detail below. Other point set registration methods may also be used in registration processes within the scope of this disclosure.

Other registration methods for use with image-guided surgery often involve the use of technologies based on electromagnetic or impedance sensing. Metallic objects or certain electronic devices used in the surgical environment may create disturbances that impair the quality of the sensed data. Other methods of registration may obstruct the clinical workflow. The systems and methods described below may perform registration based upon ICP, or another point set registration algorithm, and the calibrated movement of a point gathering instrument with, for example, a fiber optic shape sensor, thus eliminating or minimizing disruptions in the surgical environment. Other registration techniques may be used to register a set of measured points to a pre-operative model or a model obtained using another modality.

FIGS. 5A, 5B, and 5C illustrate exemplary application of processes in a segmentation method that generates a model of human lungs for registration. In some embodiments, the processes of FIGS. 5A, 5B, and/or 5C may correspond to portions of processes 452 and/or 454 of FIG. 4. FIG. 5A illustrates segmented model 502 of a set of anatomic passageways created from pre-operative or intra-operative imaging data. As shown, the passageways are airways of a human lung. Due to naturally occurring limitations or to limitations set by an operator, segmented model 502 may not include all of the passageways present within the human lungs. For example, relatively narrow and/or distal passageways of the lungs may not be fully included in segmented model 502. Segmented model 502 may be a three-dimensional model, such as a mesh model, that including the walls defining the interior lumens or passageways of the lungs.

Based on segmented model 502, centerline segmented model 504 may be generated as shown in FIG. 5B. Centerline segmented model 504 may include a set of three-dimensional straight lines or a set of curved lines that correspond to the approximate center of the passageways contained in segmented model 502. The higher the resolution of segmented model 502, the more accurately the set of straight or curved lines will correspond to the center of the passageways. Representing the lungs with centerline segmented model 504 may provide a smaller set of data that is more efficiently processed by one or more processors or processing cores than the data set of segmented model 502, which represents the walls of the passageways. In this way the functioning of a control system using the model, such as control system 112, may be improved. As shown in FIG. 5B, centerline segmented model 504 includes several branch points, some of which are highlighted for visibility in FIG.

5B. Branch points A, B, C, D, and E are shown at each of several of the branch points. Branch point A may represent the point in the model at which the trachea divides into the left and right main bronchi. The right main bronchus may be identified in the centerline segment model 504 as being located between branch points A and B. Similarly, secondary bronchi are identified by branch points B and C and between branch points B and E. Another generation of passageways may be defined between branch points C and D. Each of these generations of passageways may be associated with a representation of the diameter of the lumen of the corresponding passageway. In some embodiments, centerline model 504 may include an average diameter value of each passageway. The average diameter value may be a patient-specific value or a more general value derived from multiple patients.

In some embodiments, segmented model 502 may be used to produce centerline segment 504 or another suitable model including a cloud, set, or collection of points as follows. When segmented model 502 comprises a mesh representing the internal surfaces of one or more passageways, a subset of vertices of a mesh as represented in a stored data file including segmented model 502 may be used. Alternatively, a geometric center of voxels that represent volumes or the passageways in segmented model 502 may be used. Additionally, combinations of various approaches may be used to generate a first set of points, such as centerline segment model 504. For example, a subset of vertices of the mesh may be used along with the geometric center of voxels from the model.

In some embodiments, centerline segmented model 504 is represented in data as a cloud, set, or collection of points in three-dimensional space, rather than as continuous lines. FIG. 5C illustrates centerline segmented model 504 as a set of points 506. Each of the points of the set of model points may include coordinates such as a set of XM, YM, and ZM, coordinates, or other coordinates that identify the location of each point in the three-dimensional space. In some embodiments, each of the points may include a generation identifier that identifies which passageway generation the points are associated with and/or a diameter or radius value associated with that portion of the centerline segmented model 504. In some embodiments, information describing the radius or diameter associated with a given point may be provided as part of a separate data set.

After centerline segmented model 504 is generated and stored as the set of points 506 shown in FIG. 5C, centerline segmented model 504 may be retrieved from data storage for use in an image-guided surgical procedure. In order to use centerline segmented model 504 in the image-guided surgical procedure, centerline segmented model 504 may be registered to associate the modeled passageways in centerline segmented model 504 with the patient's actual anatomy as present in a surgical environment. Use of the model 504 in point set registration includes using the set of points 506 from centerline segmented model 504.

FIGS. 6A and 6B are exemplary side views of a patient coordinate space including a medical instrument mounted on an insertion assembly. As shown in FIGS. 6A and 6B, a surgical environment 600 includes a patient P is positioned on platform 602. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 600, a point gathering instrument 604 is coupled to an instrument carriage 606. In some embodiments, point gathering instrument 604 may use EM sensors, shape-sensors, and/or other sensor modalities. Instrument carriage 606 is mounted to an insertion stage 608 fixed within surgical environment 600. Alternatively, insertion stage 608 may be movable but have a known location (e.g., via a tracking sensor or other tracking device) within surgical environment 600. Instrument carriage 606 may be a component of a manipulator assembly (e.g., manipulator assembly 102) that couples to point gathering instrument 604 to control insertion motion (i.e., motion along the A axis) and, optionally, motion of a distal end 618 of an elongate device 610 in multiple directions including yaw, pitch, and roll. Instrument carriage 606 or insertion stage 608 may include actuators, such as servomotors, (not shown) that control motion of instrument carriage 606 along insertion stage 608.

Elongate device 610 is coupled to an instrument body 612. Instrument body 612 is coupled and fixed relative to instrument carriage 606. In some embodiments, an optical fiber shape sensor 614 is fixed at a proximal point 616 on instrument body 612. In some embodiments, proximal point 616 of optical fiber shape sensor 614 may be movable along with instrument body 612 but the location of proximal point 616 may be known (e.g., via a tracking sensor or other tracking device). Shape sensor 614 measures a shape from proximal point 616 to another point such as distal end 618 of elongate device 610. Point gathering instrument 604 may be substantially similar to medical instrument system 200.

A position measuring device 620 provides information about the position of instrument body 612 as it moves on insertion stage 608 along an insertion axis A. Position measuring device 620 may include resolvers, encoders, potentiometers, and/or other sensors that determine the rotation and/or orientation of the actuators controlling the motion of instrument carriage 606 and consequently the motion of instrument body 612. In some embodiments, insertion stage 608 is linear. In some embodiments, insertion stage 608 may be curved or have a combination of curved and linear sections.

FIG. 6A shows instrument body 612 and instrument carriage 606 in a retracted position along insertion stage 608. In this retracted position, proximal point 616 is at a position L0 on axis A. In this position along insertion stage 608 an A component of the location of proximal point 616 may be set to a zero and/or another reference value to provide a base reference to describe the position of instrument carriage 606, and thus proximal point 616, on insertion stage 608. With this retracted position of instrument body 612 and instrument carriage 606, distal end 618 of elongate device 610 may be positioned just inside an entry orifice of patient P. Also in this position, position measuring device 620 may be set to a zero and/or the another reference value (e.g., I=0). In FIG. 6B, instrument body 612 and instrument carriage 606 have advanced along the linear track of insertion stage 608 and distal end 618 of elongate device 610 has advanced into patient P. In this advanced position, the proximal point 616 is at a position L1 on the axis A. In some examples, encoder and/or other position data from one or more actuators controlling movement of instrument carriage 606 along insertion stage 608 and/or one or more position sensors associated with instrument carriage 606 and/or insertion stage 608 is used to determine the position Lx of proximal point 616 relative to position L0. In some examples, position Lx may further be used as an indicator of the distance or insertion depth to which distal end 618 of elongate device 610 is inserted into the passageways of the anatomy of patient P.

Embodiments of the point gathering instrument 604 may collect measured points using any number of modalities, including EM sensing and shape-sensing. As the measurement points are collected from within the passageways of patient P, the points are stored in a data storage device, such as a memory. The set of measured points may be stored in a database that includes at least some, but may include all, of the measured points obtained during the procedure or immediately before the procedure. As stored in memory, each of the points may be represented by data comprising coordinates of the point, a timestamp, and/or a relative sensor position or individual sensor ID (when multiple sensors distributed along a length of the point gathering instrument 604 are used to determine the location of several points simultaneously). In some embodiments, data representing each point may also include a respiratory phase marker that indicates the respiratory phase of the patient P in which the point was collected.

FIG. 6C is an exemplary side view of patient P in a patient coordinate space including an endotracheal tube (ET) 622. As shown in FIG. 6C, elongate device 610 is inserted through ET tube 622 in order to access one or more passageways of the anatomy of patient P. In some examples, known information about a bend or curvature in ET tube 622 may optionally be used to help locate the position of distal end 618 relative to proximal point 616. In some examples, even when an exact bend or curvature of ET tube 622 is not known, general knowledge about the bend or curvature of ET tube 622 may aid it determining the position of distal end 618 relative to proximal point 616 and/or registering location data collected using elongate device 610 to model information for the passageways of the anatomy of patient P. In some examples, an interior surface 623 of ET tube 622 may optionally include a distinctive color, marking, and/or pattern that may be detectable by an imaging device, such as an endoscopic camera, located at or near distal end 618 of elongate device 610. As distal end 618 enters and/or exits ET tube 622, the change in the distinctive color, marking, and/or pattern relative to interior colors and/or patterns of the passageways may help provide useful location data for distal end 618 and/or elongate device 610.

FIG. 7 is a flowchart illustrating an exemplary method 700 of providing guidance for an image-guided surgical procedure on a patient in a surgical environment, such as surgical environment 600. And although method 700 is described generally in the context of a procedure involving the airways of lungs, it is understood that method 700 is applicable to other anatomical passageways (e.g., blood vessels, ducts, calyces, and/or the like), anatomical passageways in a non-surgical context (e.g., passageways of cadavers, simulated anatomical structures, and/or the like), veterinary passageways, and/or non-medical passageways (e.g., pipes, conduit, ducts, corridors, wells, caves, mines, and/or the like). The method 700 is illustrated in FIG. 7 as a set of operations or processes 702-726. Not all of the illustrated processes 702-726 may be performed in all embodiments of method 700. Additionally, one or more processes that are not expressly illustrated in FIG. 7 may be included before, after, in between, or as part of the processes 702-726. In some embodiments, one or more of the processes 702-726 of method 700 may be implemented, at least in part, in the form of executable code stored on non-transitory, tangible, machine-readable media that when run by one or more processors (e.g., the processors of control system 112) may cause the one or more processors to perform one or more of the processes 702-724.

At a process 702, a relative position and/or orientation of a sensor reference point along an insertion path is calibrated using a position measuring device. In some examples, the proximal point 616 may optionally correspond to the sensor reference point and point gathering instrument 604 of FIGS. 6A and 6B may optionally be used to determine a position and/or orientation of proximal point 616 as instrument carriage 606 moves from a retracted position with proximal point 616 at location $L_0$ to an inserted position with proximal point 616 at location $L_1$. The calibration of proximal point 616 includes determining the direction of the movement of proximal point 616 for each change in position measuring device 620 along axis A. In the embodiments of FIGS. 6A and 6B, where the insertion stage 608 restricts movement of instrument carriage 606 to a linear path, the calibration includes determining the motion along axis A. Using the slope of insertion stage 608 and the position along axis A, the position and orientation of proximal point 616 in surgical environment 600 is determined for each corresponding measurement of position measuring device 620. In some embodiments, where an insertion stage has a curved or otherwise non-linear shape, the calibration includes determining, based on the non-linear shape and the movement of the instrument carriage 606, the position and orientation of proximal point 616 in surgical environment 600. In some examples, calibration of proximal point 616 may optionally be determined by holding distal end 618 of elongate device 610 at a fixed position while instrument carriage 606 is moved along instrument stage 608 and shape sensor 614 is used to determine the geometrical relationship between distal end 618 and proximal point 616. By taking several readings as instrument carriage 606 is moved along instrument stage 608, the position and orientation data collected by shape sensor 614 for proximal point 616 can be correlated with data from position measuring device 620 to calibrate the position and/or orientation of proximal point 616.

At a process 704, passageways of a patient are traversed and location data along the passageways is recorded. An instrument, such as an elongate device, is inserted into and then is moved or traversed along passageways of interest. As the instrument is traversed along the passageways, the position of one or more points associated with the instrument, such as a distal end of the instrument, are monitored and recorded. In the examples of FIGS. 6A and 6B, when distal end 618 of elongate device 610 is traversed along the passageways of patient P, such as along the airways of the lungs of patient P, data from shape sensor 614 and/or one or more other sensors, such as an EM sensor, on elongate device 610 is used to determine the location of distal end 618 and/or other points associated with elongate device 610. This location data may include, and/or be processed to obtain, a set of measured points as described in further detail below. In some examples, selection of the passageways to traverse may optionally be controlled by steering distal end 618 as elongate device 610 is advanced into the passageways using movement of instrument carriage 606 along instrument stage 608. In some examples, the steering of distal end 618 may optionally be controlled via teleoperational, manual, and/or automated control, such as by using master assembly 106, to survey and obtain location data for a portion of the passageways. In some examples, the steering of distal end 618 may optionally include adjusting a roll, a pitch, and/or a yaw of distal end 618, such as is described with respect to the dashed line depictions 219 of distal end 218 in FIG. 2A. As distal end 618 of elongate device 610 is moved within the passageways, the location of the distal end 618 and/or other points associated with elongate device 610 are gathered at multiple positions of distal end 618 and/or elongate device 610. In some embodiments when the passageways correspond to airways of lungs, distal end 618 of elongate device 610 may be extended up to at least 75 mm or farther into the passageways. In some examples, distal end 618 of elongate device 610 may optionally be extended through or into three or more branched generations on each side of the lung. The number of generations accessible with elongate device 610 may increase as the diameter of elongate device 610 decreases and/or as the flexibility of elongate device 610 increases.

FIG. 8 illustrates exemplary location data collected by traversing airways in human lungs. As shown in FIG. 8, location data collected by process 704 and/or method 800 is depicted by data points D. In some examples, the data points D may be stored in memory as data sets or point pools with coordinates, timestamps, sensor IDs, anatomic phase information, insertion depth, and/or the like. The data points D may correspond to location data for distal end 618 and/or other points associated with elongate device 610 collected using shape sensor 614 and/or one or more other sensors as distal end 618 is advanced into and/or retracted from the passageways being traversed. In the examples of FIGS. 6A and 6B, the location of a given collected data point DX in surgical environment 600 is determined by combining information from position measuring device 620 and the shape data from shape sensor 614 and/or one or more other sensors when distal end 618 and/or some other point associated with elongate device 610 is located at the point DX. In some examples, the position Lx of proximal point 616 along instrument stage 608 as aided by the calibration of process 702 and data from shape sensor 614 may optionally be used to determine the location of point DX. The location in the surgical environment coordinate space for the data points D becomes a reference set of location data for the passageways that can be registered with location data from a model of the passageways as is described in further detail below.

Referring back to FIG. 7, at a process 706, model information for the passageways is received. In some examples, pre-operative and/or intra-operative images of the passageways, such as the images obtained using process 542, may be used to construct the model of the passageways. In some examples, the model of the passageways may be generated by segmenting the pre-operative and/or intra-operative images using processes 454. In some examples, the model information for the passageways may correspond to the centerline segmented model 504 as described in FIG. 5C. In some embodiments, the model information may further include one or more approximate measurements for one or more features of the passageways. In some examples, when the passageways correspond to airways in lungs, the one or more approximate measurements may include a length of a trachea, a length of the right main bronchus, a length of the left main bronchus, a radius of a largest airway, and/or the like.

At a process 708, landmark locations for the passageways is recorded. In some examples, one or more of the gathered data points D may correspond to one or more landmark locations within the passageways. In some examples, the gathered data points D that correspond to the one or more landmark locations may optionally be used to seed a registration process, such as an ICP process. In some examples, each of the gathered data points D that corresponds to the one or more landmark locations may be referred to as seed points. In some examples, the gathered data points D that correspond to the one or more landmark locations may be tagged with a landmark indicator when those data points D are stored in memory. In some examples, the one or more landmark locations may correspond to branch points in the passageways. In some examples, when the passage ways are airways in lungs, the one or more landmark locations may correspond to carinas within the lungs.

In some examples, designation of the data points D as corresponding to the one or more landmark locations may occur as a result of input from an operator, such as operator O, and/or through one of more other approaches and/or automated algorithms. In some examples, the operator may designate data points D as corresponding to the one or more landmark locations by pressing a button, a pedal, a lever, issuing a command recognizable with voice recognition, and/or the like and/or activating an appropriate input control on a master assembly, such as master assembly 106. In some examples, the operator may navigate the distal end of the elongate device to a point in proximity to one of the landmark locations and initiate physical contact between the distal end and a wall of the passageways. In some examples, a torque sensor and/or an encoder for an actuator controlling the distal end may register resistance and/or a force against the distal end due to the contact with the wall of the passageway and trigger the tagging of the current location of the distal end as a landmark location. In some examples, a touch sensor, such as a capacitive and/or a Hall effect sensor, may be positioned near the distal end of the elongate device to provide an indication when the distal end is close to or in contact with the wall of the passageways and trigger the tagging of the current location of the distal end as a landmark location.

In some examples, when the distal end of the elongate device is passed through an ET tube, such as ET tube 622, a known bend or curvature of the ET tube may aid in the identification of one or more of the landmark locations. In some examples, even when the bend or curvature in the ET tube is not precisely known, the bend or curvature may be sufficiently distinctive to be identified as corresponding to a specific region of the passageways, such as the upper respiratory track and trachea because a more proximal portion of the elongate device at a proximal end of the ET tube forms a nearly 90° angle with respect to a more distal portion of the elongate device at a distal end of the ET tube. Based on pose information of the proximal point of the elongate device and the curvature of the ET tube, which may be easily identified using the shape sensor, the trachea of the patient may be identified and used as one of the landmark locations. In some examples, detection and location of the distal end of the ET tube, such as by detecting the end of a distinctive color, marking, and/or pattern of an interior surface of the ET tube, may further aid in identifying a landmark location within the trachea of the patient.

According to some embodiments, when the orientation of the patient relative to the proximal point of the elongate device is known, navigation of the distal end of the elongate device to the left or the right may help identify one or more landmark locations associated with the left and/or right main bronchus. In some examples, data from the shape sensor and/or other sensor may optionally be used to identify the roughly right angle between the proximal end and the distal end of the ET tube created by the curvature of the ET tube, with the distal end of the ET tube identifying a possible landmark location within the trachea of the patient. In some examples, the roughly right angle may optionally be used to identify a first plane that bisects the anatomy of the patient into right and left halves. As the distal end is further steered into either the left or right main bronchus, a second angle defining a second plane may be identified, which is roughly orthogonal to the first plane. The orientation of the first and second planes may then be used to determine one or more additional landmark locations.

FIG. 9 illustrates exemplary landmark locations for airways in human lungs 900. As shown in the frontal cross-section view of FIG. 9, human lungs 900 include passageways in the form of airways 910. In some embodiments, each of the airways 910 may be modeled using a centerline model 920 indicated by the dashed lines throughout the airways 910. In some examples, centerline model 920 may be consistent with centerline segmented model 504. In human lungs, the trachea and the left and right main bronchi are often good choices for landmark locations as they are typically traversed early during exploration of airways 910, are located at relatively low insertion depths, and/or are located before too many branch points in the airways 910. As shown, the trachea branches at main carina $C_2$ into the left and right main bronchi with the right and left main bronchi extending from main carina $C_2$ to carinas $C_1$ and $C_3$, respectively. A first landmark location 930 is associated with a center point of the airways 910 near main carina $C_2$ where the trachea branches into the right and left main bronchi. A second landmark location 940 is located in the trachea along centerline model 920. In some examples, the distance between first landmark location 930 and second landmark location 940 may be determined based on the length of trachea included in the model information received during process 706. In some examples, where the human lungs 900 correspond to a typical sized adult, second landmark location 940 may be located up to 30 mm proximal to first landmark location 930. A third landmark location 950 is located in the left main bronchus along centerline model 920. In some examples, the distance between first landmark location 930 and third landmark location 950 may be determined based on the length of the left main bronchus included in the model information received during process 706. In some examples, where the human lungs 900 correspond to a typical sized adult, third landmark location 950 may be located up to 30 mm distal to first landmark location 930. A fourth landmark location 960 is located in the right main bronchus along centerline model 920. In some examples, the distance between first landmark location 930 and fourth landmark location 960 may be determined based on the length of the right main bronchus included in the model information received during process 706. In some examples, where the human lungs 900 correspond to a typical sized adult, fourth landmark location 960 may be located up to 30 mm distal to first landmark location 930.

Determination of the landmark locations, such as landmark locations 930-960, may occur using a two phase approach. The first phase can include building a tree representative of the human lung passageways while the second phase can include locating landmarks within the tree. The second phase will be described in detail below in reference to FIG. 12. In the first phase, the location data recorded during process 704 is analyzed and the tree that roughly corresponds to the passageways is determined. The tree may either be constructed in a top-down fashion beginning with the location data point with the shallowest (e.g., smallest) insertion depth and then evaluating each of the other location data points based on insertion depth to build the tree using relative distances between the location data points.

Alternatively, as is further discussed below with respect to FIGS. 10 and 11, the tree may be constructed in a bottom-up fashion beginning with the location data point with the deepest (e.g., largest) insertion depth and then evaluating each of the other location data points based on insertion depth to build the tree using relative distances between the location data points. Once the passageway tree is identified, the landmark locations may be extracted from the passageway tree, as is discussed in further detail below with respect to FIG. 12.

FIG. 10 illustrates a flowchart of an exemplary method 1000 of building a passageway tree in location data. And although method 1000 is described generally in the context of a procedure involving the airways of lungs, it is understood that method 1000 is applicable to other anatomical passageways (e.g., blood vessels, ducts, calyces, and/or the like), anatomical passageways in a non-surgical context (e.g., passageways of cadavers, simulated anatomical structures, and/or the like), veterinary passageways, and/or non-medical passageways (e.g., pipes, conduit, ducts, corridors, wells, caves, mines, and/or the like). The method 1000 is illustrated in FIG. 10 as a set of operations or processes 1002-1014. Not all of the illustrated processes 1002-1014 may be performed in all embodiments of method 1000. Additionally, one or more processes that are not expressly illustrated in FIG. 10 may be included before, after, in between, or as part of the processes 1002-1014. In some embodiments, one or more of the processes 1002-1014 of method 1000 may be implemented, at least in part, in the form of executable code stored on non-transitory, tangible, machine-readable media that when run by one or more processors (e.g., the processors of control system 112) may cause the one or more processors to perform one or more of the processes 1002-1014. And although FIG. 10 is described with respect to location data points, one or ordinary skill would understand that method 1000 and processes 1004-1014 may be equally applied to cluster centers when clustering is used.

At a process 1002, location data is organized by insertion depth. In some embodiments, the location data recorded during process 704 may be organized as it is collected by placing each of the location data points into bins based on ranges of the insertion depth. Once organized into bins, the location data in each bin may then be optionally clustered (to separate location data collected from different passageways) based on location, with the location data in each cluster being aggregated, such as by averaging, to obtain an aggregate location or cluster center for the cluster. In some examples, a clustering algorithm such as the K-means algorithm and/or the mean-shift algorithm may be used to create the clusters. In some examples, a size of each cluster may optionally be limited so that each cluster includes only location data within a threshold distance of the cluster center. In some examples, the threshold distance may optionally be configurable based on a type of passageway being traversed, a positional accuracy in determining the location of the distal end of the elongate device, and/or the like. In some examples, the threshold distance may optionally be set according to the radius of the largest airway included in the model information received during process 706 and/or set to approximately 5 mm.

In some embodiments, the location data recorded during process 704 for the distal end of the elongate device is alternatively organized by sorting the location data and/or the bins using the insertion depth recorded along with the location of each of the points in the location data. In some examples, the location data may be sorted using a sorting algorithm, such as a bubble sort or similar algorithm after it is recorded and/or optionally sorted as it is recorded during process 704 using an insertion sort or similar algorithm.

At a process 1004, the location data is analyzed to identify the location data point with the deepest (e.g., largest) inser-tion depth. This location data point typically corresponds to the deepest insertion of the elongate device into the pas-sageways and is representative of a first leaf in the passage-way tree.

At a process 1006, a next deepest location data point is identified and is referred to below as the currently evaluated location data point.

At a process 1008, all the previously evaluated location data points that are within a threshold distance of the currently evaluated location data point are identified. A distance, such as the Euclidean distance, between the cur-rently evaluated location data point and each of the location data points analyzed thus far (i.e., each of the location data points with a greater insertion depth) is computed and each of the previously evaluated location data points that are within the threshold distance of the currently evaluated location data point are identified. In some examples, the threshold distance may optionally be configured based on one or more of a type of passageway being traversed, a positional accuracy in determining the location of the distal end of the elongate device, age and/or size of a patient, and/or the like. In some examples, the threshold distance may be set according to the radius of the largest airway included in the model information received during process 706 and/or set to approximately 5 mm. Because location data points in different passageways of the passageway tree may have the same or approximately the same insertion depth, location data from one branch of the passageway tree are separated from location data from other branches of the passageway tree that have an overlap in insertion depth using process 1008.

At a process 1010, it is determined whether any previ-ously evaluated location data points are located within the threshold distance of the currently evaluated location data point. When one or more nearby previously evaluated loca-tion data points are found, these location data points are used to construct one or more parent-child relationships in the passageway tree using a process 1012. When no nearby previously evaluated location data points are found, the current location data point is processed as if it is located at a deepest insertion point in a passageway branch different than a passageway of the closest location data point using a process 1014.

At the process 1012, the currently evaluated location data point is linked as a parent to the closest location data point in at most two branches of the passageway tree. The cur-rently evaluated location data point is first recorded as a parent node in the passageway tree to the node associated with the nearest of the location data points determined during process 1008 to be within the threshold distance. If any other location data points are identified during process 1008 to be within the threshold distance, the currently evaluated location data point is also recorded as a parent node in the passageway tree to the nearest one of the other location data points. These parent-child relationships build up the passageway tree so that it reflects the tree structure of the passageways. When there are further location data points to process, the next deepest location data point is evaluated by returning to process 1006.

At the process 1014, the currently evaluated location data point is used to create a new leaf node in the passageway tree. When the current location data point is not within the threshold distance of any of the previously evaluated loca-tion data points, the currently evaluated location data point is assumed to correspond to a previously unknown branch in the passageway tree and the new leaf node is recorded to represent a deepest point on the previously unknown branch. When there are further location data points to process, the next deepest location data point is evaluated by returning to process 1006.

As discussed above and further emphasized here, FIG. 10 is merely an example which should not unduly limit the scope of the claims. One of ordinary skill in the art would recognize many variations, alternatives, and modifications. In some embodiments, insertion and retraction of the elon-gate device, such as by monitoring a velocity of the insertion depth, may optionally be used to reduce and/or simplify the comparisons and analysis of processes 1006-1014. In some examples, detecting transitions from retraction to insertion may optionally be used to help identify the various branches in the passageway tree and/or establish parent-child rela-tionships in the nodes of the passageway tree.

FIG. 11A illustrates application of the method 1000 on exemplary location data 1100 to generate the passageway tree 1150 of FIG. 11B. In the example of FIGS. 11A and 11B, the location data 1100, as depicted by a point "x", is shown after being organized according to process 1002. And although the location data 1100 is shown in two-dimensions, it is understood that the location data 1100 may also be representative of three-dimensional. Additionally, the loca-tion data 1100 has been organized into bins 1101-1109 based on insertion depth, with the boundaries between bins 1101-1109 being depicted by the dashed arcs. The location data 1100 in each of the bins 1101-1109 has been further orga-nized into clusters with each cluster being shown by an approximately circular cluster boundary and a cluster center depicted by a center "o". And although the clusters are shown with one, two, three, or four location data points "x", it is understood that other clusters (not shown) may include five or more location data points "x".

Once the location data 1100 has been organized using process 1002, a deepest location data point, or in this example a deepest cluster center, is identified using process 1004. As shown the deepest cluster center corresponds to cluster 1111. This deepest cluster becomes the basis for leaf node 1151 in passageway tree 1150. The remaining cluster centers found in location data 1100 are then considered in order of insertion depth (deepest to shallowest) by processes 1006-1014.

In a first application of process 1006, the cluster center for cluster 1112 is identified as the next deepest cluster center and becomes the currently evaluated cluster center. During process 1008 no previously evaluated cluster centers are found within the threshold distance of the cluster center for cluster 1112, so cluster 1112 because the basis for a new leaf node 1152 using process 1014.

In a second application of process 1006, the cluster center for cluster 1113 is identified as the next deepest cluster center and becomes the currently evaluated cluster center. During process 1008, the cluster center for cluster 1111 is identified as the only previously evaluated cluster center that is within the threshold distance, so by application of process 1012, cluster 1113 becomes the basis for node 1153, which is linked as a parent to node 1151 using parent-child link 1161.

In a third application of process 1006, the cluster center for cluster 1114 is identified as the next deepest cluster center and becomes the currently evaluated cluster center. During process 1008, the cluster center for cluster 1112 is identified as the only previously evaluated cluster center that is within the threshold distance, so by application of process 1012, cluster 1114 becomes the basis for node 1154, which is linked as a parent to node 1152 using parent-child link 1162.

In a fourth application of process 1006, the cluster center for cluster 1115 is identified as the next deepest cluster center and becomes the currently evaluated cluster center. During process 1008 no previously evaluated cluster centers are found within the threshold distance of the cluster center for cluster 1115, so cluster 1115 because the basis for a new leaf node 1155 using process 1014.

In a fifth application of process 1006, the cluster center for cluster 1116 is identified as the next deepest cluster center and becomes the currently evaluated cluster center. During process 1008, the cluster centers for cluster 1113 and 1114 are both identified as being previously evaluated cluster centers that are within the threshold distance, so by application of process 1012, cluster 1116 becomes the basis for node 1156, which is linked as a parent to node 1153 using parent-child link 1163 and as a parent to node 1154 using parent-child link 1164 because the cluster centers for clusters 1113 and 1114 are the two previously evaluated cluster centers that are nearest to the cluster center for cluster 1116 and within the threshold distance.

Processes 1006-1014 are then further repeated until the cluster center for cluster 1117 is evaluated as the next deepest cluster center and becomes the basis for head node 1157 of passageway tree 1150.

As previously described, landmark determination can be determined in two phases including the first phase represented by method 1000 and the second phase shown in FIG. 12. FIG. 12 illustrates a flowchart of an exemplary method 1200 of identifying landmark locations in a passageway tree which can be built using the method 1000 of FIG. 10. And although method 1200 is described generally in the context of a procedure involving the airways of lungs, it is understood that method 1200 is applicable to other anatomical passageways (e.g., blood vessels, ducts, calyces, and/or the like), anatomical passageways in a non-surgical context (e.g., passageways of cadavers, simulated anatomical structures, and/or the like), veterinary passageways, and/or non-medical passageways (e.g., pipes, conduit, ducts, corridors, wells, caves, mines, and/or the like). The method 1200 is illustrated in FIG. 12 as a set of operations or processes 1202-1208. Not all of the illustrated processes 1202-1208 may be performed in all embodiments of method 1200. Additionally, one or more processes that are not expressly illustrated in FIG. 12 may be included before, after, in between, or as part of the processes 1202-1208. In some embodiments, one or more of the processes 1202-1208 of method 1200 may be implemented, at least in part, in the form of executable code stored on non-transitory, tangible, machine-readable media that when run by one or more processors (e.g., the processors of control system 112) may cause the one or more processors to perform one or more of the processes 1202-1208.

At the process 1202, a main branch point is identified. Using the passageway tree determined using method 1000 and knowledge regarding the type and nature of the passageways, the main branch point in the passageways is determined. In some embodiments, when the passageways correspond to airways in lungs, the main branch point corresponds to a branch in the airways at the main carina, such as corresponds to first (or most proximal) landmark location 930 in the examples of FIG. 9. In some examples, the main branch point is a first node of the passageway tree (e.g., a first node of the passageway tree with two children) that meets certain criteria. In some examples, the main branch point may correspond to a first node of the passageway tree with two children that are themselves the head nodes of two sufficiently large sub-trees. In some examples, the two sub-trees are sufficiently large when the two sub-trees are approximately balanced (e.g., one of the sub-trees includes no more than 50 percent more nodes than the other) and have a sufficient depth (i.e., have a minimum number of parent-child levels, such as 10 or more, to the deepest leaf node in the respective sub-tree). In some examples, the main branch point is a first node of the passageway tree beyond a minimum threshold insertion depth (e.g., a first node in the passageway tree with two children and having a corresponding insertion depth larger than the minimum threshold insertion depth). In some examples, by setting criteria for the main branch point, process 1202 reduces the likelihood of one or more false branches caused by sensor noise, location data accidently collected in a tracheal bronchus (such as in lungs of a pig where the first branch does not correspond to the main carina and a split into the right and left main bronchi), and/or the like. In some examples, the minimum threshold insertion depth is an insertion depth beyond a distal end of a recognizable point, such as a distal end of an ET tube. In some examples, the minimum threshold insertion depth may optionally be configured based on one or more of a type of passageway being traversed, a positional accuracy in determining the location of the distal end of the elongate device, age and/or size of a patient, and/or the like. In some examples, the minimal threshold insertion depth may be determined based on the length of trachea included in the model information received during process 706. In some examples, where the passageways correspond to airways of a typical sized adult, the minimum threshold insertion depth may be proximal to the first landmark a distance based on the smallest of 30 mm, a maximum distance from the main carina, and/or a trachea length in the lungs based on a volumetric scan. In some examples, a location of the main branch point is determined by aggregating, such as by averaging, the location data for each of the nodes, both parent and children, of the passageway tree within a threshold insertion depth of the node corresponding to the main branch point. In some examples, the threshold insertion depth may optionally be approximately 5 mm. In some examples, the aggregating may reduce errors in determining the location of the main branch point due to noise in the location data collected during process 704 and/or increase a likelihood that the location determined for the main branch point is closer to a centerline of the passageways at the main branch point.

At a process 1204, a proximal landmark location is identified. In some embodiments, when the passageways correspond to airways in lungs, the proximal landmark location corresponds to a point in the trachea above the main carina, such as corresponds to second landmark location 940 in the examples of FIG. 9. One or more nodes in the passageway tree having an insertion depth a desired insertion depth proximal to the insertion depth of the main branch point (i.e., above the main branch point in the passageway tree) are used to determine the proximal landmark location. In some examples, the proximal landmark location is determined using a node having an insertion depth that is closest to being the desired insertion depth more proximal than the insertion depth of the main branch point. In some examples, the proximal landmark location is determined by aggregating, such as by averaging, the location data for each of the one or more nodes of the passageway tree within a threshold insertion depth of the desired insertion depth more proximal than the insertion depth of the main branch point. In some examples, the desired insertion depth proximal to the insertion depth of the main branch point may optionally be configured based on one or more of a type of passageway being traversed, a positional accuracy in determining the location of the distal end of the elongate device, age and/or size of a patient, and/or the like. In some examples, the desired insertion depth located proximal to the insertion depth of the main branch point based on the length of the trachea included in the model information received during process 706. In some examples, where the passageways correspond to airways in lungs of an adult-sized human, the desired insertion depth may be located up to 30 mm proximal to the main branch point. In some examples, the threshold insertion depth may optionally be approximately 5 mm. In some examples, the aggregating may reduce errors in determining the location of the proximal landmark location due to noise in the location data collected during process 704 and/or increase a likelihood that the location determined for the proximal landmark location is closer to a centerline of the passageways proximal to the main branch point.

At a process 1206, a first branch landmark location is identified. In some embodiments, when the passageways correspond to airways in lungs, the first branch landmark location corresponds to a point in either the left or right main bronchus below (or distal to) the main carina, such as corresponds to third landmark location 950 or fourth landmark location 960 in the examples of FIG. 9. In some examples, the first branch landmark location is located in a first branch of the passageway tree distal to the main branch point. One or more nodes in the passageway tree having an insertion depth a desired insertion depth distal to the insertion depth of the main branch point (i.e., below the main branch point in the passageway tree and along one of the branches corresponding to one of the children of the node corresponding to the main branch point) are used to determine the first branch landmark location. In some examples, the first branch landmark location is determined using a node having an insertion depth that is closest to being the desired insertion depth more distal than the insertion depth of the main branch point. In some examples, the first branch landmark location is determined by aggregating, such as by averaging, the location data for each of the one or more nodes of the passageway tree within a threshold insertion depth of the desired insertion depth more distal than the insertion depth of the main branch point. In some examples, the desired insertion depth distal to the insertion depth of the main branch point may optionally be configured based on one or more of a type of passageway being traversed, a positional accuracy in determining the location of the distal end of the elongate device, age and/or size of a patient, and/or the like. In some examples, the desired insertion depth is located distal to the insertion depth of the main branch point based on the length of the right or left bronchus included in the model information received during process 706. In some examples, where the passageways correspond to airways of human lungs for an adult-sized human, the desired insertion depth may be located up to 30 mm distal to the main branch point. In some examples, the threshold insertion depth may optionally be approximately 5 mm. In some examples, the aggregating may reduce errors in determining the location of the first branch landmark location due to noise in the location data collected during process 704 and/or increase a likelihood that the location determined for the first branch landmark location is closer to a centerline of the passageways in the first branch.

At a process 1208, a second branch landmark location is identified. In some embodiments, when the passageways correspond to airways in lungs, the second branch landmark location corresponds to a point in either the right or left main bronchus below the main carina, such as corresponds to fourth landmark location 960 or third landmark location 950 in the examples of FIG. 9. In some examples, the second branch landmark location is located in a second branch of the passageway tree distal to the main branch point that is different from the first branch of the passageway tree used to determine the first branch landmark location during process 1206. One or more nodes in the passageway tree having an insertion depth a desired insertion depth distal to the insertion depth of the main branch point (i.e., below the main branch point in the passageway tree and along the other of the branches corresponding to the other of the children of the node corresponding to the main branch point) are used to determine the second branch landmark location. In some examples, the second branch landmark location is determined using a node having an insertion depth that is closest to being the desired insertion depth more distal than the insertion depth of the main branch point. In some examples, the second branch landmark location is determined by aggregating, such as by averaging, the location data for each of the one or more nodes of the passageway tree within a threshold insertion depth of the desired insertion depth more distal than the insertion depth of the main branch point. In some examples, the desired insertion depth distal to the insertion depth of the main branch point may optionally be configured based on one or more of a type of passageway being traversed, a positional accuracy in determining the location of the distal end of the elongate device, age and/or size of a patient, and/or the like. In some examples, the desired insertion depth is located distal to the insertion depth of the main branch point based on the length of the right or left bronchus included in the model information received during process 706. In some examples, where the passageways correspond to airways of human lungs for an adult-sized human, the desired insertion depth may be located up to 30 mm distal to the main branch point. In some examples, the threshold insertion depth may optionally be approximately 5 mm. In some examples, the aggregating may reduce errors in determining the location of the second branch landmark location due to noise in the location data collected during process 704 and/or increase a likelihood that the location determined for the second branch landmark location is closer to a centerline of the passageways in the second branch.

According to some embodiments, several possible approaches may optionally be used to determine whether the first branch landmark location and/or the second branch landmark location are located in a left branch below the main branch point (e.g., corresponding to a landmark location in the left main bronchus) or located in a right branch below the main branch point (e.g., corresponding to a landmark location in the right main bronchus). In some examples, identification of the left and right branches may optionally be determined based on timestamps associated with the location data used to determine the first and second branch landmark locations when the left and right branches are known to be traversed in a predetermined order, such as traversing the left branch before traversing the right branch. In some examples, identification of the left and right branches may optionally be determined based on the timestamps associated with the location data used to determine the first and second landmark locations and one or more steering commands for the elongate device that were time stamped and recorded as the elongate device was navigated into the first and second branches. In some examples, a direction of the one or more steering commands used before the corresponding location data is collected can be used to determine whether the first branch or the second branch is the left or right branch. In some examples, a known left or right orientation of the sensor system may optionally be used to determine which of the first and second branch landmark locations is located more to the left and which is located more to the right. In some examples, the left or right orientation of the system may be determined from an anterior and/or posterior orientation of the sensor data based on the shape of the passage proximal to the main branch point, such as may be inferred from location data associated with the mouth and/or nose of the patient and/or the curvature of an ET tube. In some examples, angles between a direction of the proximal landmark location relative to the main branch point and directions to the first and second branch landmark locations relative to the main branch point may optionally be used to determine the left and right branches. In some examples, the left and right passageways are determined based the determination of an anterior and/or posterior direction of the sensor data based on the shape of the passage proximal to the airway tree (e.g., by determination of a location of a mouth and nose proximal to the airway tree). In some examples, when the passageways correspond to airways of human lungs, an angle between the directions to the trachea and the left main bronchus from the main carina is smaller than an angle between the directions to the trachea and the right main bronchus from the main carina. In some examples, a length of the first and second branches from the main branch point to a next more distal branch in the first and second branches may optionally be used to determine the left and right branches. In some examples, when the passageways correspond to airways of human lungs, a length of the left main bronchus is longer than a length of the right main bronchus. In some embodiments, combinations of two or more of these approaches may optionally be used to determine whether the first and second branch landmark locations are located in left or right branches of the passageways.

Even though the identification of the landmark locations is described using location data collected using an elongate device during process 704, in some embodiments, methods 1000 and/or 1200 may optionally be adapted to identify landmark locations in data collected using other approaches, such as data collected from two-dimensional and/or three-dimensional medical imaging. In some examples, the two phase process of generating a passageway tree from collected location data, such as location data from a volumetric three-dimensional scan, followed by the extraction of landmark locations from the passageway tree may also be applies to pre-operative and/or intra-operative scans.

Referring back to FIG. 7, at a process 710, an initial seed transformation between the landmark locations and the model information for the passageways is determined. According to some embodiments, use of a suitable seed transformation for close point registration algorithms, such as ICP often result in better registration and/or faster convergence for the close point algorithm. In some examples, the transformation that maps between at least three non-collinear landmark locations identified in the landmark locations during process 708 and/or method 1000 and the corresponding locations in the model information received during process 706 often provides a good seed transformation for close point registration between the location data collected during process 704 and the model information (for example, locations described with reference to FIG. 9 such as the trachea, left main bronchi, and right main bronchi) received during process 706. In some examples, the initial seed transformation may optionally be a rigid transform in which each of the data points D for the landmark locations are transformed by the same coordinate transformation that maps positions and orientations from a coordinate system or coordinate frame of the location data collected during process 704 and a coordinate system or coordinate frame for the model information received during process 706. In some examples, the initial seed transformation may optionally be a non-rigid transformation where each of the data points D for the landmark locations are transformed by different coordinate transformations. In some examples, the initial seed transformation may be modeled as a homogenous transform that can translate and/or rotate 3D points from one coordinate system to another. In some examples, multiple initial seed transformations determined using different landmark locations and/or different combinations of landmark locations may optionally be compared with the initial seed transformation having the smallest error when mapping between the coordinate system of the location data collected during process 704 and the coordinate system for the model information received during process 706 being selected as the initial seed transformation. In some examples, the second, third, and fourth landmark locations determined during method 1000 may optionally be used to determine the initial seed transformation.

At an optional process 712, the initial seed transformation is applied to the recorded location data. Using the rigid or non-rigid transformation determined during process 710, the location data collected and recorded during process 704 is transformed to place the points in the location data in closer alignment with corresponding points in the model information received during process 706. In some examples, when the initial seed transformation is a homogeneous transformation, the transformation of the location data is accomplished by applying the initial seed transformation to each of the points in the location data using matrix multiplication.

At a process 714, the location data recoded during process 704 and/or method 800 is registered to the model information received during process 706. Process 714 is shown as an iterative process that includes repeated application of processes 716-722 until convergence between the location data and the model information is obtained. In some examples, the iterative processes of process 714 correspond to the ICP registration technique. FIG. 9 illustrates an exemplary post registration alignment of two sets of points resulting from application of process 714 to the location data as collected and shown in FIG. 8. In some embodiments, the location data used during the registration may optionally be limited to location data collected during a particular anatomic phase (or a range of anatomic phases) so as to limit the effects of noise introduced in the collected data by changes in the anatomic phase.

At a process 716, points in the location data are matched to points in the model information. Transformation of the points in the location data using the initial seed transformation during process 712 and/or by the transformation of process 720 as described further below typically brings the points in the location data into better positional and/or rotational alignment with corresponding points in the model information. However, because initial iterations to bring the points in the location data in alignment with corresponding points in the model information do not always identify the correct correspondence between the points in the location data and the points in the model information, rematching to update the correspondence is performed. Each of the points in the location data, as transformed, is matched to a point in the model information that is closest to the point in the location data. In some examples, the closest point in the model information may be determined by iterating through each of the points in the model information and finding the point that has a shortest Euclidean distance to the point in the location data being matched. In some examples, other techniques, such as KD trees and/or the like may optionally be used to more efficiently perform the matching. In some examples, some matches may be discarded based on a maximum distance threshold determination, a maximum angle threshold determination, and/or other metrics employed to filter out matches that are not deemed to be reliable enough or "close" enough for inclusion in the transformation determined during a process 718 as is described further below.

At the process 718, a further transformation is determined. Based on the matching of process 716, the further transformation identifies an additional transformation to the location data to bring the location data into further alignment with the model information. In some examples, the further transformation determines a displacement and/or rotation, such as in the form of a homogenous transformation, which would best bring the matched points into alignment. In some examples, the further transformation is determined by computing an overall and/or an aggregated offset in position and orientation between the points matched during process 716. In some examples, the further transformation may be limited such that a maximum offset and/or a maximum rotation is applied during any iteration of process 714. In some examples the maximum offset and/or the maximum rotation may optionally be scaled based on a number of iterations of process 714 that have been performed.

At a process 720, the further transformation is applied to the location data. Using the further transformation determined during process 718, the location data as transformed by process 712 and/or prior applications of process 720 is further transformed to place the location data in closer alignment with the points in the model information received during process 706. In some examples, when the further transformation is a homogeneous transformation, the further transformation of the location data is accomplished by applying the further transformation to each of the points in the location data using matrix multiplication.

At a process 722, the convergence of the registration technique is evaluated. In some examples, error measures between the locations of the points in the location data and the locations of the points in the model information are computed that assess an overall difference between the location data as transformed and the model information. When the error measures in aggregate are greater than a threshold value, additional iterations of processes 716-722 are repeated until the overall error measures fall below the threshold value. A result of this process is illustrated in FIG. 13 showing how multiple iterations of processes 716-722 are able to bring the location data as represented by points D in FIG. 8 into alignment with the points in anatomic model information 550. In some examples, a number of iterations to converge between FIG. 8 and FIG. 13 may vary based on differences between the model information and the actual point locations in the location data, the convergence threshold, and/or the like.

In some embodiments, the progression of processes 716-722 may optionally be displayed to an operator, such as operator O, by displaying images similar to FIGS. 8 and 9 on a user interface display. In some examples, the operator may optionally monitor the registration to determine when adequate convergence is achieved. In some examples, the registration of processes 716-722 may optionally be repeated during a surgical procedure such as at regular intervals, as additional location data is obtained, when the patient is moved, and/or the like.

After the registration is complete, an image-guided surgical procedure may, optionally, be performed. In some examples, the model information may identify one or more intervention sites and/or targeted locations in the anatomy of the patient to which a targeted procedure is to be applied. In some examples, a composite transformation including the initial seed transformation determined during process 710 and each of the further transformations determined during process 718 may be used to map current location data for the distal end of the elongate device to a corresponding location in the model information to aid the operator in planning and/or executing a motion plan to move the distal end of the elongate device from its current location to one of the targeted locations. As shown in FIG. 7, the image-guided surgical procedure may correspond to optional processes 724 and 726.

At the optional process 724, a current location of the distal end of the elongate device is determined. In some examples, the location of the proximal point and data from the shape sensor may be used to determine the current location of the distal end of the elongate device where a surgical instrument can be applied to the anatomy of the patient by inserting the surgical instrument through the elongate device. In some examples, other sensors, such as the EM sensor may optionally be used to determine the current location of the distal end of the elongate device.

At the optional process 726, the distal end of the elongate device is located in the model information. Using the composite transformation determined by processes 702-722, the current location of the distal end of the elongate device determined during process 724 may be transformed so that the location of the distal end of the elongate device, and thus the surgical instrument may be determined relative to the model information. Once the location of the distal end of the elongate device is known within the passageways as described in the model information, it is possible for the operator and/or an automated system to plan and/or execute a motion plan to deliver the surgical instrument to one of the targeted locations. As the plan is executed, processes 724 and 726 may be repeated to continually update the current location of the distal end of the elongate device and the motion plan.

As discussed above and further emphasized here, FIG. 7 is merely an example which should not unduly limit the scope of the claims. One of ordinary skill in the art would recognize many variations, alternatives, and modifications. In some embodiments, the transformation of processes 712 and/or 720 may be applied in different ways. In some examples, the initial seed transformation and/or the further transformation may optionally be defined to transform the points in the model information so that they are in closer alignment with the points in the location data with the initial seed transformation and/or the further transformation being applied to transform the model information rather than the location data. In some examples, the initial seed transformation and/or the further transformation may optionally be divided into separate transformations designed to transform both the location data and the model information toward a common coordinate system.

One or more elements in embodiments of the invention (e.g., the processes of methods 700, 1000, and/or 1200) may be implemented in software to execute on a processor of a computer system, such as control system 112. When implemented in software, the elements of the embodiments of the invention are essentially the code segments to perform the necessary tasks. The program or code segments can be stored in a non-transitory machine-readable storage media, including any media that can store information including an optical medium, semiconductor medium, and magnetic medium. Machine-readable storage media examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A device, comprising:
an instrument usable to collect location data for one or more passageways; and
one or more processors coupled to the instrument;
wherein the one or more processors are configured to:
organize a plurality of points within the location data based on a corresponding insertion depth of the instrument when each of the plurality of points is collected;
create a passageway tree based on the organized points, wherein to create the passageway tree the one or more processors are further configured to:
iterate through the plurality of points in descending order of insertion depth; and
create parent-child relationships between nodes of the passageway tree corresponding to the points based on distances between the points;
identify at least three non-collinear landmark locations within the passageway tree;
create a seed transformation between one or more of the at least three non-collinear landmark locations and corresponding model locations in model data; and
register, using the seed transformation, the plurality of points to the model data for the one or more passageways.

2. The device of claim 1, wherein the instrument is a flexible catheter comprising a shape sensor, wherein the location data is provided by the shape sensor.

3. The device of claim 2, wherein the shape sensor is a fiber optic shape sensor.

4. The device of claim 1, further comprising a tracking sensor coupled to the instrument.

5. The device of claim 1, wherein to organize the plurality of points within the location data the one or more processors are further configured to:
place the plurality of points into bins based on ranges of insertion depth; and
cluster the plurality of points within each bin based on distances between points in each of the bins.

6. The device of claim 1, wherein to create the passageway tree the one or more processors are further configured to link a first node corresponding to a first point as a first parent to a second node corresponding to a second point closest to the first point that also has a greater insertion depth than the first point.

7. The device of claim 1, wherein to create the passageway tree the one or more processors are further configured to link a first node corresponding to a first point as a parent to each of a second node and a third node, the second and third node corresponding to two closest points to the first point that also have a greater insertion depth than the first point.

8. The device of claim 1, wherein to create the passageway tree the one or more processors are further configured to create a leaf node corresponding to a first point when the first point is not within a threshold distance of any point having a greater insertion depth than the first point.

9. The device of claim 1, wherein to identify the at least three non-collinear landmark locations within the passageway tree, the one or more processors are further configured to:
identify a main branch point in the passageway tree;
identify a first landmark location proximal to the main branch point;
identify a second landmark location distal to the main branch point in a first branch of the passageway tree distal to the main branch point; and
identify a third landmark location distal to the main branch point in a second branch of the passageway tree distal to the main branch point, the second branch being different from the first branch.

10. The device of claim 9, wherein the one or more processors are further configured to determine a location of the main branch point based on an aggregation of the location data corresponding to each of the points within a threshold distance of the main branch point.

11. The device of claim 9, wherein the one or more processors are further configured to determine a location of the first landmark location based on the location data corresponding to a point located at a first insertion depth proximal to the main branch point, the first insertion depth being a desired distance proximal from a second insertion depth of the main branch point.

12. The device of claim 9, wherein the one or more processors are further configured to determine a location of the first landmark location based on an aggregation of the location data corresponding to each of the points having a first insertion depth within a range of desired distances proximal to a second insertion depth of the main branch point.

13. The device of claim 9, wherein the one or more processors are further configured to determine a location of the second landmark location based on the location data corresponding to a point in the first branch located at a first insertion depth distal to the main branch point, the first insertion depth being a desired distance distal from a second insertion depth of the main branch point.

14. The device of claim 9, wherein the one or more processors are further configured to determine whether the first branch is a left branch or a right branch in the passageway tree based on an order in which the first branch is traversed, steering commands of the instrument recorded when the location data is collected, one or more of an orientation angle and a length of the first branch, or a known left-right orientation of a sensor system used by the instrument to collect the location data.

15. The device of claim 9, wherein the main branch point is a most proximal node of the passageway tree having two children.

16. The device of claim 1, wherein the passageways correspond to airways of lungs.

17. A method of registration using one or more processors, the method comprising:

collecting a set of sensor data during insertion of a flexible elongate device within a plurality of passageways, wherein the sensor data comprises a plurality of points representing a plurality of locations of the flexible elongate device within the plurality of passageways;

organizing the plurality of points based on a corresponding insertion depth of the flexible elongate device when each of the plurality of points is collected;

creating a passageway tree based on the organized points by:

iterating through the plurality of points in descending order of insertion depth; and creating parent-child relationships between nodes of the passageway tree corresponding to the points based on distances between the points;

identifying at least three non-collinear landmark locations within the passageway tree;

creating a seed transformation between one or more of the at least three non-collinear landmark locations and corresponding model locations in model data;

registering, using the seed transformation, the plurality of points to the model data for the plurality of passageways; and based on the registering and in response to one or more received user inputs, moving the flexible elongate device within one or more of the plurality of passageways.

18. The method of claim 17, wherein identifying the at least three non-collinear landmark locations comprises:

identifying a main branch point in the passageway tree;

identifying a first landmark location proximal to the main branch point;

identifying a second landmark location distal to the main branch point in a first branch of the passageway tree, wherein the first branch is distal to the main branch point; and identifying a third landmark location distal to the main branch point in a second branch of the passageway tree, wherein the second branch is distal to the main branch point, the second branch being different from the first branch.

19. The method of claim 17, wherein identifying the at least three non-collinear landmark locations comprises identifying a main branch point in the passageway tree.

20. A non-transitory machine-readable medium comprising a plurality of machine-readable instructions which when executed by one or more processors associated with a device are adapted to cause the one or more processors to perform operations including:

collecting a set of sensor data during insertion of a flexible elongate device within a plurality of passageways, wherein the sensor data comprises a plurality of points representing a plurality of locations of the flexible elongate device within the plurality of passageways;

organizing the plurality of points based on a corresponding insertion depth of the flexible elongate device when each of the plurality of points is collected;

creating a passageway tree based on the organized points by:

iterating through the plurality of points in descending order of insertion depth; and creating parent-child relationships between nodes of the passageway tree corresponding to the points based on distances between the points;

identifying at least three non-collinear landmark locations within the passageway tree;

creating a seed transformation between one or more of the at least three non-collinear landmark locations and corresponding model locations in model data;

registering, using the seed transformation, the plurality of points to the model data for the plurality of passageways; and based on the registering and in response to one or more received user inputs, moving the flexible elongate device within one or more of the plurality of passageways.

* * * * *